United States Patent
Geiss et al.

(10) Patent No.: US 9,087,391 B2
(45) Date of Patent: Jul. 21, 2015

(54) DETERMINING AN IMAGE CAPTURE PAYLOAD BURST STRUCTURE

(71) Applicant: Google Inc., Mountain View, CA (US)

(72) Inventors: Ryan Geiss, Mountain View, CA (US); Samuel William Hasinoff, Mountain View, CA (US)

(73) Assignee: Google Inc., Mountain View, CA (US)

( * ) Notice: Subject to any disclaimer, the term of this patent is extended or adjusted under 35 U.S.C. 154(b) by 69 days.

(21) Appl. No.: 13/713,734

(22) Filed: Dec. 13, 2012

(65) Prior Publication Data

US 2014/0168474 A1   Jun. 19, 2014

(51) Int. Cl.
G06T 5/50 (2006.01)
H04N 5/235 (2006.01)
H04N 5/335 (2011.01)
H04N 5/355 (2011.01)

(52) U.S. Cl.
CPC ............... *G06T 5/50* (2013.01); *H04N 5/2355* (2013.01); *H04N 5/35554* (2013.01); *G06T 2207/10144* (2013.01); *G06T 2207/20221* (2013.01)

(58) Field of Classification Search
None
See application file for complete search history.

(56) References Cited

U.S. PATENT DOCUMENTS

| | | | |
|---|---|---|---|
| 4,644,582 A | 2/1987 | Morishita et al. | |
| 5,781,308 A | 7/1998 | Fujii et al. | |
| 5,828,793 A | 10/1998 | Mann | |
| 5,926,190 A | 7/1999 | Turkowski et al. | |
| 6,061,091 A | 5/2000 | Van de Poel et al. | |
| 6,075,905 A | 6/2000 | Herman et al. | |
| 6,101,285 A | 8/2000 | Fan | |
| 6,204,881 B1 | 3/2001 | Ikeda et al. | |
| 6,539,116 B2 | 3/2003 | Takaoka | |
| 6,693,718 B1 | 2/2004 | Takaoka | |
| 6,925,121 B1 | 8/2005 | Komiya et al. | |
| 6,975,755 B1 | 12/2005 | Baumberg | |
| 7,098,946 B1 * | 8/2006 | Koseki et al. | ............ 348/229.1 |
| 7,173,666 B1 | 2/2007 | Masaki et al. | |
| 7,239,805 B2 | 7/2007 | Uyttendaele et al. | |
| 7,626,614 B1 | 12/2009 | Marcu | |

(Continued)

FOREIGN PATENT DOCUMENTS

| | | |
|---|---|---|
| JP | 2005-045804 | 2/2005 |
| JP | 2012-029029 | 2/2012 |

(Continued)

OTHER PUBLICATIONS

Final Office Action, U.S. Appl. No. 13/863,981 mailed Apr. 8, 2014, 26 pages.

(Continued)

*Primary Examiner* — Timothy J Henn
*Assistant Examiner* — Quan Pham
(74) *Attorney, Agent, or Firm* — McDonnell Boehen Hulbert & Berghoff LLP

(57) ABSTRACT

A first plurality of images of a scene may be captured. Each image of the first plurality of images may be captured using a different TET. Based at least on the first plurality of images, a long TET, a short TET, and a TET sequence that includes the long TET and the short TET may be determined. A second plurality of images of the scene may be captured. The images in the second plurality of images may be captured sequentially in an image sequence using a sequence of TETs corresponding to the TET sequence. Based on one or more images in the image sequence, an output image may be constructed.

22 Claims, 8 Drawing Sheets

(56) References Cited

U.S. PATENT DOCUMENTS

| | | | |
|---|---|---|---|
| 7,667,764 B2 | 2/2010 | Kamon et al. | |
| 7,840,093 B2 | 11/2010 | Fu et al. | |
| 7,903,168 B2 | 3/2011 | Pillman et al. | |
| 7,924,321 B2 | 4/2011 | Nayar et al. | |
| 7,940,325 B2 | 5/2011 | Kim et al. | |
| 7,944,485 B2 | 5/2011 | Ovsiannikov | |
| 8,023,004 B2 | 9/2011 | Asoma | |
| 8,059,891 B2 | 11/2011 | Li et al. | |
| 8,072,507 B2 | 12/2011 | Fuh et al. | |
| 8,094,211 B2 | 1/2012 | Kwon et al. | |
| 8,200,020 B1 | 6/2012 | Geiss et al. | |
| 8,208,048 B2 | 6/2012 | Lin et al. | |
| 8,237,813 B2 | 8/2012 | Garten | |
| 8,406,560 B2 | 3/2013 | Lee et al. | |
| 8,411,962 B1 | 4/2013 | Geiss et al. | |
| 8,446,481 B1 | 5/2013 | Geiss et al. | |
| 8,576,295 B2 | 11/2013 | Ito | |
| 8,866,927 B2 * | 10/2014 | Levoy et al. | 348/222.1 |
| 8,866,928 B2 | 10/2014 | Geiss et al. | |
| 8,885,976 B1 | 11/2014 | Kuo et al. | |
| 2001/0019362 A1 | 9/2001 | Nakamura et al. | |
| 2003/0002750 A1 | 1/2003 | Ejiri et al. | |
| 2003/0095192 A1 | 5/2003 | Horiuchi | |
| 2004/0160525 A1 | 8/2004 | Kingetsu et al. | |
| 2005/0147322 A1 | 7/2005 | Saed | |
| 2005/0163380 A1 | 7/2005 | Wang et al. | |
| 2005/0239104 A1 | 10/2005 | Ferea et al. | |
| 2005/0243176 A1 | 11/2005 | Wu et al. | |
| 2006/0269155 A1 | 11/2006 | Tener et al. | |
| 2006/0291740 A1 | 12/2006 | Kim et al. | |
| 2007/0003261 A1 | 1/2007 | Yamasaki | |
| 2007/0147824 A1 | 6/2007 | Hamamura | |
| 2008/0094486 A1 * | 4/2008 | Fuh et al. | 348/229.1 |
| 2008/0253758 A1 | 10/2008 | Yap et al. | |
| 2008/0278633 A1 | 11/2008 | Tsoupko-Sitnikov et al. | |
| 2008/0298717 A1 | 12/2008 | Lee | |
| 2009/0040364 A1 | 2/2009 | Rubner | |
| 2009/0123082 A1 | 5/2009 | Atanssov et al. | |
| 2009/0185622 A1 | 7/2009 | Itoh et al. | |
| 2009/0207258 A1 | 8/2009 | Jang et al. | |
| 2009/0222625 A1 | 9/2009 | Ghosh et al. | |
| 2009/0231445 A1 | 9/2009 | Kanehiro | |
| 2009/0231449 A1 | 9/2009 | Tzur et al. | |
| 2009/0231468 A1 | 9/2009 | Yasuda | |
| 2009/0244301 A1 | 10/2009 | Border et al. | |
| 2009/0268963 A1 | 10/2009 | Kang et al. | |
| 2009/0274387 A1 | 11/2009 | Jin | |
| 2009/0322901 A1 | 12/2009 | Subbotin et al. | |
| 2010/0066858 A1 | 3/2010 | Asoma | |
| 2010/0103194 A1 | 4/2010 | Chen et al. | |
| 2010/0150473 A1 | 6/2010 | Kwon et al. | |
| 2010/0157078 A1 | 6/2010 | Atanassov et al. | |
| 2010/0165075 A1 | 7/2010 | Chou et al. | |
| 2010/0166337 A1 | 7/2010 | Murashita et al. | |
| 2010/0265357 A1 | 10/2010 | Liu et al. | |
| 2010/0277631 A1 | 11/2010 | Sugiyama | |
| 2010/0321539 A1 | 12/2010 | Ito | |
| 2010/0328490 A1 | 12/2010 | Kurane et al. | |
| 2010/0328491 A1 | 12/2010 | Ovsiannikov | |
| 2011/0047155 A1 | 2/2011 | Sohn et al. | |
| 2011/0069200 A1 * | 3/2011 | Oh et al. | 348/229.1 |
| 2011/0085697 A1 | 4/2011 | Clippard et al. | |
| 2011/0149111 A1 | 6/2011 | Prentice et al. | |
| 2011/0200265 A1 | 8/2011 | Prigent | |
| 2011/0222793 A1 | 9/2011 | Ueda et al. | |
| 2011/0228993 A1 | 9/2011 | Reilly et al. | |
| 2011/0254976 A1 | 10/2011 | Garten | |
| 2011/0279706 A1 | 11/2011 | Lesiak et al. | |
| 2012/0002082 A1 | 1/2012 | Johnson et al. | |
| 2012/0002898 A1 | 1/2012 | Cote et al. | |
| 2012/0002899 A1 | 1/2012 | Orr, IV et al. | |
| 2012/0044381 A1 | 2/2012 | Jannard et al. | |
| 2012/0050557 A1 | 3/2012 | Atanassov et al. | |
| 2012/0105681 A1 | 5/2012 | Morales | |
| 2012/0127348 A1 | 5/2012 | Li | |
| 2012/0189197 A1 | 7/2012 | Li et al. | |
| 2012/0201426 A1 | 8/2012 | Jasinski et al. | |
| 2012/0201450 A1 | 8/2012 | Bryant et al. | |
| 2012/0201456 A1 | 8/2012 | El-Mahdy et al. | |
| 2012/0219235 A1 | 8/2012 | Solhusvik et al. | |
| 2012/0249828 A1 | 10/2012 | Sun | |
| 2012/0308126 A1 | 12/2012 | Hwang et al. | |
| 2012/0314100 A1 | 12/2012 | Frank | |
| 2013/0033616 A1 | 2/2013 | Kaizu et al. | |
| 2013/0083216 A1 | 4/2013 | Jiang et al. | |
| 2013/0100314 A1 | 4/2013 | Li et al. | |
| 2013/0121569 A1 | 5/2013 | Yadav | |
| 2013/0329092 A1 * | 12/2013 | Wong | 348/241 |
| 2014/0042233 A1 | 2/2014 | Yang | |
| 2014/0219578 A1 | 8/2014 | Peng et al. | |

FOREIGN PATENT DOCUMENTS

| | | |
|---|---|---|
| KR | 10-2007-0085867 | 8/2007 |
| KR | 10-0911814 | 8/2009 |
| KR | 10-2010-0086987 | 8/2010 |
| WO | 98/02844 | 1/1998 |
| WO | 2004/098167 | 11/2004 |
| WO | 2011/093994 | 8/2011 |
| WO | 2011/102850 | 8/2011 |
| WO | 2012/027290 | 3/2012 |
| WO | 2012/039669 | 3/2012 |
| WO | 2012/061261 | 5/2012 |
| WO | 2012/098842 | 7/2012 |
| WO | 2012/110894 | 8/2012 |

OTHER PUBLICATIONS

Office Action, U.S. Appl. No. 13/713,720, mailed Apr. 8, 2014, 46 pages.

International Search Report and Written Opinion for PCT/US2014/011498 mailed Apr. 22, 2014, 11 pages.

Office Action for U.S. Appl. No. 13/759,749 mailed Sep. 24, 2014, 38 pages.

International Searching Authority, International Search Report and Written Opinion for International Application No. PCT/US2014/038963 mailed Sep. 17, 2014, 12 pages.

Office Action for U.S. Appl. No. 13/718,533 mailed Apr. 22, 2014, 48 pages.

Office Action for U.S. Appl. No. 13/863,981 mailed Jun. 24, 2014, 23 pages.

Notice of Allowance for U.S. Appl. No. 13/718,533 mailed Jul. 18, 2014, 9 pages.

Notice of Allowance for U.S. Appl. No. 13/713,720 mailed Jul. 18, 2014, 13 pages.

Office Action for U.S. Appl. No. 13/863,981 mailed Oct. 7, 2013, 45 pages.

Office Action for U.S. Appl. No. 13/849,824 mailed Nov. 5, 2014, 14 pages.

Notice of Allowance for U.S. Appl. No. 13/610,288 mailed Feb. 28, 2013, 31 pages.

International Searching Authority, International Search Report and Written Opinion for PCT/US2013/071618 mailed Mar. 3, 2014.

International Searching Authority, International Search Report and Written Opinion for PCT/US2013/072569 mailed Mar. 6, 2014.

Notice of Allowance for U.S. Appl. No. 13/305,389 mailed Feb. 22, 2012, 9 pages.

Notice of Allowance for U.S. Appl. No. 13/458,334 mailed Oct. 11, 2012, 34 pages.

Notice of Allowance for U.S. Appl. No. 13/743,565 mailed Dec. 2, 2014, 15 pages.

Notice of Allowance for U.S. Appl. No. 14/455,444 mailed Oct. 2, 2014, 9 pages.

Office Action for U.S. Appl. No. 13/902,254 mailed Dec. 2, 2014, 9 pages.

Office Action for U.S. Appl. No. 13/902,267 mailed Dec. 12, 2014, 12 pages.

Nayar et al., "Adaptive Dynamic Range Imaging: Optical Control of Pixel Exposures Over Space and Time," Proceedings of the Ninth IEEE International Conference on Computer Vision (ICCV'03), 2003, pp. 1-8.

(56) References Cited

OTHER PUBLICATIONS

Duan et al., "Tone-mapping High Dynamic Range Images by Novel Histogram Adjustment," Pattern Recognition, 2010, 39 pages, vol. 43, No. 5.
"Exposure (photography)," Wikipedia, the free encyclopedia, Jun. 21, 2012, pp. 1-8 (http://en.wikipedia.org/wiki/Autoexposure#Automatic_exposure).
"JPEG," Wikipedia, the free encyclopedia, Jul. 31, 2012, pp. 1-16 (http://en.wikipedia.org/wiki/JPEG).
"High dynamic range imaging," Wikipedia, the free encyclopedia, Jun. 21, 2012, pp. 1-11 (http://en.wikipedia.org/wiki/High_dynamic_range_imaging).
"Tone mapping," Wikipedia, the free encyclopedia, Jun. 21, 2012, pp. 1-10 (http://en.wikipedia.org/wiki/Tone_mapping).
"Metering mode," Wikipedia, the free encyclopedia, Jun. 25, 2012, pp. 1-3 (http://en.wikipedia.org/wiki/Metering_mode).
"YCbCr," Wikipedia, the free encyclopedia, Jul. 31, 2012, pp. 1-5 (http://en.wikipedia.org/wiki/YCbCr).
Lowe, D.G., "Object Recognition from Local Scale-Invariant Features," Proc. of the International Conference on Computer Vision, Sep. 20-22, 1999, pp. 1150-1157, vol. 2.
Brown, M. & Lowe, D., "Invariant Features from Interest Point Groups," Computer, (2002) p. 253-262, Available at: http://citeseerx.ist.psu.edu/viewdoc/download?doi=10.1.1.73.5616&rep=rep1&type=pdf.
Winder, S.A.J. and Brown, M., "Learning Local Image Descriptors," Computer Vision and Pattern Recognition, 2007. CVPR '07. IEEE Conference on In Computer Vision and Pattern Recognition, 2007. CVPR '07. IEEE Conference on (Jun. 2007), pp. 1-8. doi:10.1109/CVPR.2007.382971 Key: citeulike:1663569.
Sinha et al., "Feature Tracking and Matching in Video Using Programmable Graphics Hardware," Machine Vision and Applications, DOI 10.1007/s00138-007-0105-z, Nov. 2007.
Wagner et al., "Pose Tracking from Natural Features on Mobile Phones," Proceeding ISMAR '08 Proceedings of the 7th IEEE/ACM International Symposium on Mixed and Augmented Reality IEEE Computer Society Washington, DC, USA, Sep. 15-18, 2008, pp. 125-134.
Özuysal et al., "Fast Keypoint Recognition in Ten Lines of Code," Computer Vision and Pattern Recognition, IEEE Computer Society Conference on In Computer Vision and Pattern Recognition, 2007. CVPR '07. IEEE Conference on, vol. 0 (2007), pp. 1-8. doi:10.1109/CVPR.2007.383123 Key: citeulike:2943111.
Bay et al., "SURF: Speeded Up Robust Features," 9th European Conference on Computer Vision, 2008, pp. 346-359, vol. 110, No. 3.
Ta, Duy-Nguyen et al., "SURFTrac: Efficient Tracking and Continuous Object Recognition using Local Feature Descriptors," IEEE Computer Society Conference on Computer Vision and Pattern Recognition, 2009, pp. 2937-2944.
Bauer et al., "Comparing Several Implementations of Two Recently Published Feature Detectors," In Proc. of the International Conference on Intelligent and Autonomous Systems, IAV, Toulouse, France (2007).
SIFT, accessed on Oct. 21, 2011, from Wikipedia, http://en.wikipedia.org/w/index.php?title=Special:Book&bookcmd=download&collection_id=1bf75abdad524091&writer=rl&return_to=Scale-invariant+feature+transform.
SURF, accessed on Oct. 24, 2011, from Wikipedia, http://en.wikipedia.org/wiki/SURF.
Wagner et al., "Real-time detection and tracking for augmented reality on mobile phones," IEEE Trans Vis Comput Graph, May-Jun. 2010, pp. 355-368, vol. 16, No. 3.
SynthCam iPhone, https://sites.google.com/site/marclevoy/Tutorial accessed Oct. 24, 2011.
Karpenko et al., "Digital Video Stabilization and Rolling Shutter Correction using Gyroscopes," Stanford Tech Report CTSR Mar. 2011, http://graphics.stanford.edu/papers/stabilization/karpenko_gyro.pdf (Sep. 2011).
Gelfand, Natasha, et al. "Multi-exposure imaging on mobile devices." In Proceedings of the international conference on Multimedia, ACM, 2010, pp. 823-826.
Cyganek, Bogustaw, "Comparison of nonparametric transformations and bit vector matching for stereo correlation." Combinatorial Image Analysis, 2005, pp. 534-547.
Fife, Wade S. et al., "Improved Census Transforms for Resource-Optimized Stereo Vision," IEEE Transactions on Circuits and Systems for Video Technology, Jan. 2013, vol. 23, No. 1, pp. 60-73.
Hansen, Christian et al., "Chapter 1: The Image Deblurring Problem," Deblurring Images: Matrices, Spectra, and Filtering, SIAM, Philadelphia, 2006, pp. 1-12.
Seemann, Torsten et al., "Structure preserving noise filtering of images using explicit local segmentation." Fourteenth International Conference on Pattern Recognition, IEEE, 1998, vol. 2, pp. 1610-1612.
Zabih et al., "Non-parametric Local Transforms for Computing Visual Correspondence," In Proceedings of European Conference on Computer Vision, Stockholm, Sweden, May 1994, pp. 151-158.
International Searching Authority, International Search Report and Written Opinion for PCT/US2013/072638 mailed Mar. 11, 2014, 10 pages.
International Searching Authority, International Search Report and Written Opinion for PCT/US2013/071663 mailed Mar. 13, 2014, 9 pages.
International Searching Authority, International Search Report and Written Opinion for PCT/US2013/72564 mailed Mar. 11, 2014, 13 pages.
International Searching Authority, International Search Report and Written Opinion for PCT/US2013/071459 mailed Mar. 13, 2014, 9 pages.
Jin et al., "Face Detection Using Improved LBP Under Bayesian Framework," Proceedings of the Third International Conference on Image and Graphics (ICIG'04), 2004, pp. 1-4.
Mandava et al., "Speckle Noise Reduction Using Local Binary Pattern," 2nd International Conference on Communication, Computing & Security (ICCCS-2012), Procedia Technology, 2012, pp. 574-581, vol. 6.
Office Action for U.S. Appl. No. 13/743,565 mailed Sep. 4, 2014, 20 pages.
Office Action for U.S. Appl. No. 13/722,519 mailed Sep. 4, 2014, 10 pages.
Final Office Action for U.S. Appl. No. 13/863,981 mailed Dec. 24, 2014, 21 pages.
Office Action for U.S. Appl. No. 13/722,519 mailed Feb. 19, 2015, 11 pages.
Office Action for U.S. Appl. No. 14/488,891 mailed Feb. 13, 2015, 6 pages.
Office Action for U.S. Appl. No. 13/847,238 mailed Jan. 2, 2015, 6 pages.

\* cited by examiner

DETERMINING AN IMAGE CAPTURE PAYLOAD BURST STRUCTURE

BACKGROUND

Generally, imaging may refer to representing the color and brightness characteristics of digital images. Low dynamic range (LDR) imaging may represent digital images (e.g., photographs and motion video) with 8 or fewer bits for each color channel of a pixel. As a result, up to 256 levels of brightness may be supported. Currently, a wide range of video output devices (e.g., computer monitors, tablet and smartphone screens, televisions, etc.) support displaying LDR images.

However, real-world scenes often exhibit a wider range of brightness than can be represented by LDR imaging. As an example scene with a wide brightness range, consider an individual standing in a dark room in front of a window. This scene may include both extremely bright regions (e.g., sunlit features outside the window) and extremely dark regions (e.g., the features in the room). Ideally, a photograph of this scene would include both the details in the bright regions and the details in the dark regions.

SUMMARY

In a first example embodiment, a first plurality of images of a scene may be captured. Each image of the first plurality of images may be captured with a different total exposure time (TET). Based at least on the first plurality of images, a TET sequence may be determined for capturing further images of the scene. A second plurality of images of the scene may be captured. Images in the second plurality of images may be captured using the TET sequence. Based at least on the second plurality of images, an output image of the scene may be constructed.

In a second example embodiment, a first plurality of images of a scene may be captured. Each image of the first plurality of images may be captured using a different TET. Based at least on the first plurality of images, a long TET, a short TET, and a TET sequence that includes the long TET and the short TET may be determined. A second plurality of images of the scene may be captured. The images in the second plurality of images may be captured sequentially in an image sequence using a sequence of TETs corresponding to the TET sequence. Based on one or more images in the image sequence, an output image may be constructed.

A third example embodiment may include a non-transitory computer-readable storage medium, having stored thereon program instructions that, upon execution by a computing device, cause the computing device, and/or its peripherals, to perform operations in accordance with the first and/or second example embodiments.

A fourth example embodiment may include a computing device, comprising at least a processor, an image sensor, and data storage. The data storage may contain program instructions that, upon execution by the processor, cause the computing device operate in accordance with the first and/or second example embodiments.

These as well as other aspects, advantages, and alternatives will become apparent to those of ordinary skill in the art by reading the following detailed description with reference where appropriate to the accompanying drawings. Further, it should be understood that the description provided in this summary section and elsewhere in this document is intended to illustrate the claimed subject matter by way of example and not by way of limitation.

DETAILED DESCRIPTION

Figure 1:
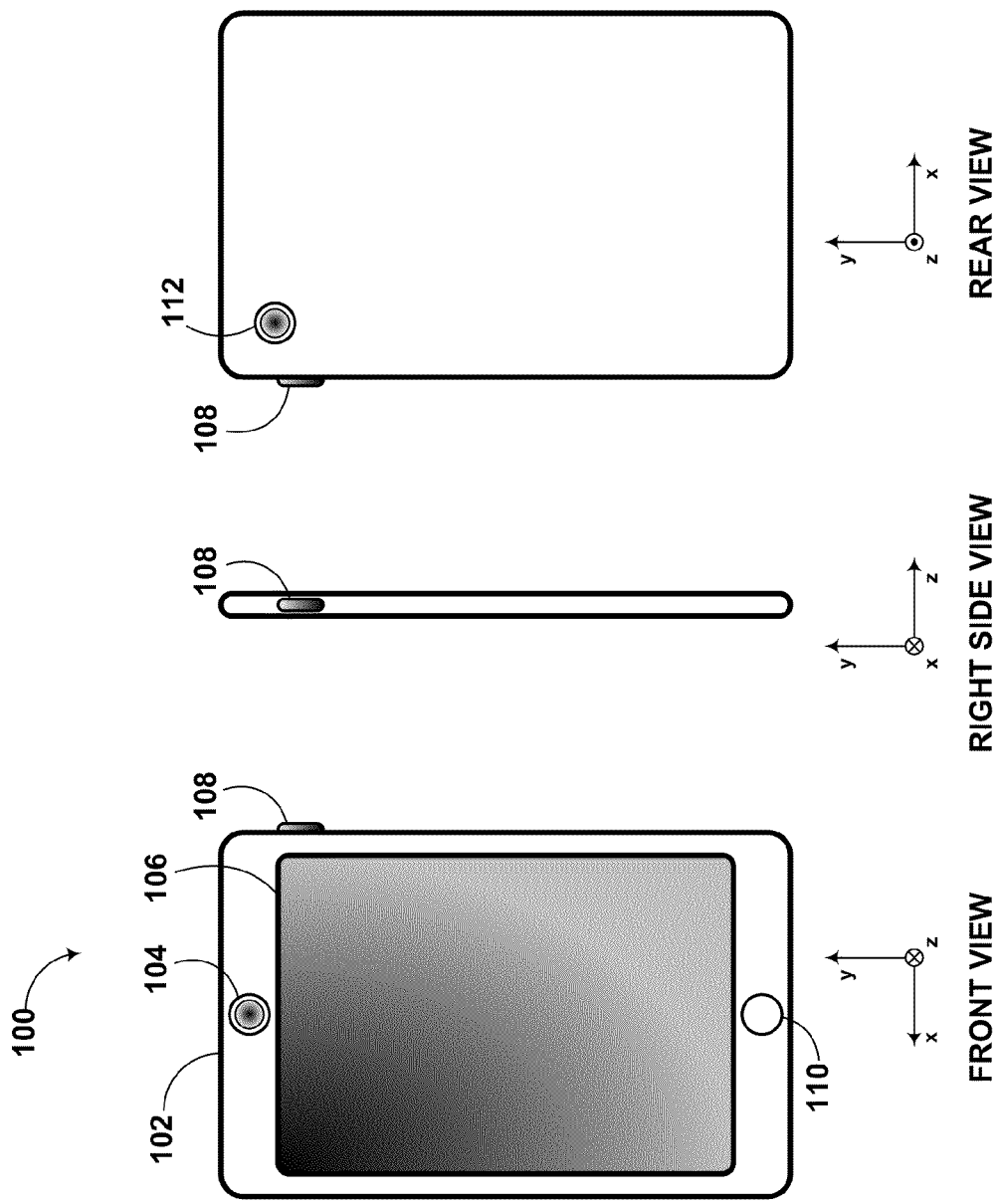
FIG. 1 depicts front, right side, and rear views of a digital camera device, in accordance with an example embodiment.

As image capture devices, such as cameras, become more popular, they may be employed as standalone hardware devices or integrated into various other types of devices. For instance, still and video cameras are now regularly included in wireless communication devices (e.g., mobile phones), tablet computers, laptop computers, video game interfaces, home automation devices, and even automobiles and other types of vehicles.

The physical components of a camera may include an aperture through which light enters, a recording surface for capturing the image represented by the light, and a lens positioned in front of the aperture to focus at least part of the image on the recording surface. The aperture may be fixed size or adjustable. In an analog camera, the recording surface may be photographic film. In a digital camera, the recording surface may include an electronic image sensor (e.g., a charge coupled device (CCD) or a complementary metal-oxide-semiconductor (CMOS) sensor) to transfer and/or store captured images in a data storage unit (e.g., memory).

A shutter may be coupled to or nearby the lens or the recording surface. The shutter may either be in a closed position, in which it blocks light from reaching the recording surface, or an open position, in which light is allowed to reach to recording surface. The position of the shutter may be controlled by a shutter button. For instance, the shutter may be in the closed position by default. When the shutter button is triggered (e.g., pressed), the shutter may change from the closed position to the open position for a period of time, known as the shutter cycle. During the shutter cycle, an image may be captured on the recording surface. At the end of the shutter cycle, the shutter may change back to the closed position.

Alternatively, the shuttering process may be electronic. For example, before an electronic shutter of a CCD image sensor is "opened" the sensor may be reset to remove any residual signal in its photodiodes. While the electronic shutter remains open, the photodiodes may accumulate charge. When or after the shutter closes, these charges may be transferred to longer-term data storage. Combinations of mechanical and electronic shuttering may also be possible.

Regardless of type, a shutter may be activated and/or controlled by something other than a shutter button. For instance, the shutter may be activated by a softkey, a timer, or some other trigger. Herein, the term "image capture" may refer to any mechanical and/or electronic shuttering process that results in one or more photographs being recorded, regardless of how the shuttering process is triggered or controlled.

The exposure of a captured image may be determined by a combination of the size of the aperture, the brightness of the light entering the aperture, and the length of the shutter cycle (also referred to as the shutter length or the exposure length). Additionally, a digital or analog gain may be applied to the image, thereby influencing the exposure. In some embodiments, the term "total exposure length" or "total exposure time" may refer to the shutter length multiplied by the gain for a particular aperture size. Herein, the term "total exposure time," or "TET," should be interpreted as possibly being a shutter length, an exposure time, or any other metric that controls the amount of signal response that results from light reaching the recording surface.

A still camera may capture one or more images each time image capture is triggered. A video camera may continuously capture images at a particular rate (e.g., 24 images—or frames—per second) as long as image capture remains triggered (e.g., while the shutter button is held down). Some digital still cameras may open the shutter when the camera device or application is activated, and the shutter may remain in this position until the camera device or application is deactivated. While the shutter is open, the camera device or application may capture and display a representation of a scene on a viewfinder. When image capture is triggered, one or more distinct digital images of the current scene may be captured.

Cameras—even analog cameras—may include software to control one or more camera functions and/or settings, such as aperture size, TET, gain, and so on. Additionally, some cameras may include software that digitally processes images during or after these images are captured. While it should be understood that the description above refers to cameras in general, it may be particularly relevant to digital cameras.

As noted previously, digital cameras may be standalone devices or integrated with other devices. As an example, FIG. 1 illustrates the form factor of a digital camera device 100. Digital camera device 100 may be, for example, a mobile phone, a tablet computer, or a wearable computing device. However, other embodiments are possible. Digital camera device 100 may include various elements, such as a body 102, a front-facing camera 104, a multi-element display 106, a shutter button 108, and other buttons 110. Digital camera device 100 could further include a rear-facing camera 112. Front-facing camera 104 may be positioned on a side of body 102 typically facing a user while in operation, or on the same side as multi-element display 106. Rear-facing camera 112 may be positioned on a side of body 102 opposite front-facing camera 104. Referring to the cameras as front and rear facing is arbitrary, and digital camera device 100 may include multiple cameras positioned on various sides of body 102.

Multi-element display 106 could represent a cathode ray tube (CRT) display, a light emitting diode (LED) display, a liquid crystal (LCD) display, a plasma display, or any other type of display known in the art. In some embodiments, multi-element display 106 may display a digital representation of the current image being captured by front-facing camera 104 and/or rear-facing camera 112, or an image that could be captured or was recently captured by either or both of these cameras. Thus, multi-element display 106 may serve as a viewfinder for either camera. Multi-element display 106 may also support touchscreen and/or presence-sensitive functions that may be able to adjust the settings and/or configuration of any aspect of digital camera device 100.

Front-facing camera 104 may include an image sensor and associated optical elements such as lenses. Front-facing camera 104 may offer zoom capabilities or could have a fixed focal length. In other embodiments, interchangeable lenses could be used with front-facing camera 104. Front-facing camera 104 may have a variable mechanical aperture and a mechanical and/or electronic shutter. Front-facing camera 104 also could be configured to capture still images, video images, or both. Further, front-facing camera 104 could represent a monoscopic, stereoscopic, or multiscopic camera. Rear-facing camera 112 may be similarly or differently arranged. Additionally, front-facing camera 104, rear-facing camera 112, or both, may be an array of one or more cameras.

Either or both of front facing camera 104 and rear-facing camera 112 may include or be associated with an illumination component that provides a light field to illuminate a target object. For instance, an illumination component could provide flash or constant illumination of the target object. An illumination component could also be configured to provide a light field that includes one or more of structured light, polarized light, and light with specific spectral content. Other types of light fields known and used to recover three-dimensional (3D) models from an object are possible within the context of the embodiments herein.

Either or both of front facing camera 104 and rear-facing camera 112 may include or be associated with an ambient light sensor that may continuously or from time to time determine the ambient brightness of a scene that the camera can capture. In some devices, the ambient light sensor can be used to adjust the display brightness of a screen associated with the camera (e.g., a viewfinder). When the determined ambient brightness is high, the brightness level of the screen may be increased to make the screen easier to view. When the determined ambient brightness is low, the brightness level of the screen may be decreased, also to make the screen easier to view as well as to potentially save power. Additionally, the ambient light sensor's input may be used to determine a TET of an associated camera, or to help in this determination.

Digital camera device 100 could be configured to use multi-element display 106 and either front-facing camera 104 or rear-facing camera 112 to capture images of a target object. The captured images could be a plurality of still images or a video stream. The image capture could be triggered by activating shutter button 108, pressing a softkey on multi-element display 106, or by some other mechanism. Depending upon the implementation, the images could be captured automatically at a specific time interval, for example, upon pressing shutter button 108, upon appropriate lighting conditions of the target object, upon moving digital camera device 100 a predetermined distance, or according to a predetermined capture schedule.

As noted above, the functions of digital camera device 100—or another type of digital camera—may be integrated into a computing device, such as a wireless communication device, tablet computer, laptop computer and so on. For purposes of example, FIG. 2 is a simplified block diagram showing some of the components of an example computing device 200 that may include camera components 224.

By way of example and without limitation, computing device 200 may be a cellular mobile telephone (e.g., a smartphone), a still camera, a video camera, a fax machine, a computer (such as a desktop, notebook, tablet, or handheld computer), a personal digital assistant (PDA), a home automation component, a digital video recorder (DVR), a digital television, a remote control, a wearable computing device, or some other type of device equipped with at least some image capture and/or image processing capabilities. It should be understood that computing device 200 may represent a physical camera device such as a digital camera, a particular physical hardware platform on which a camera application operates in software, or other combinations of hardware and software that are configured to carry out camera functions.

Figure 2:
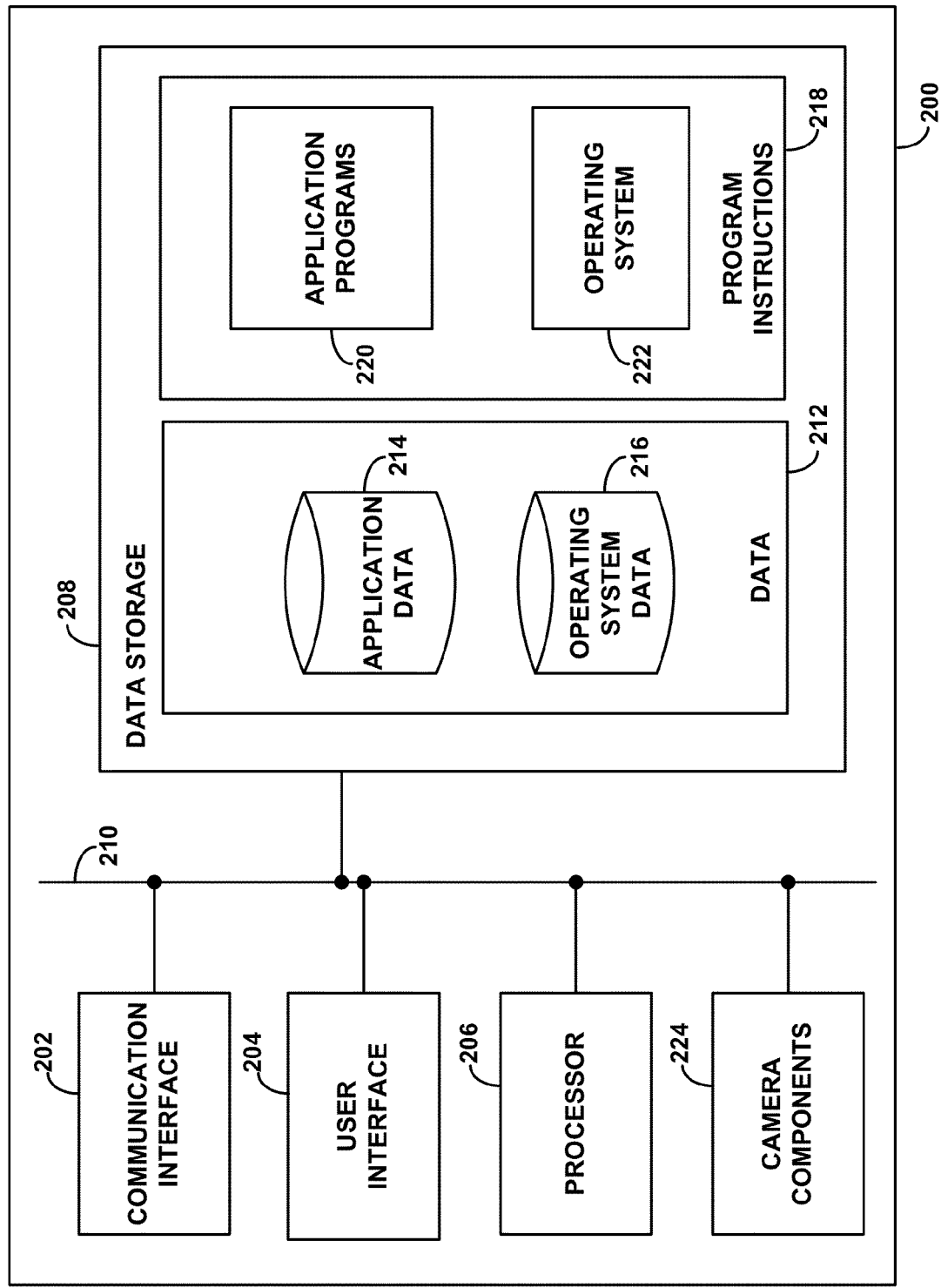
FIG. 2 depicts a block diagram of a computing device with image capture capability, in accordance with an example embodiment.

As shown in FIG. 2, computing device 200 may include a communication interface 202, a user interface 204, a processor 206, data storage 208, and camera components 224, all of which may be communicatively linked together by a system bus, network, or other connection mechanism 210.

Communication interface 202 may function to allow computing device 200 to communicate, using analog or digital modulation, with other devices, access networks, and/or transport networks. Thus, communication interface 202 may facilitate circuit-switched and/or packet-switched communication, such as plain old telephone service (POTS) communication and/or Internet protocol (IP) or other packetized communication. For instance, communication interface 202 may include a chipset and antenna arranged for wireless communication with a radio access network or an access point. Also, communication interface 202 may take the form of or include a wireline interface, such as an Ethernet, Universal Serial Bus (USB), or High-Definition Multimedia Interface (HDMI) port. Communication interface 202 may also take the form of or include a wireless interface, such as a Wifi, BLUETOOTH®, global positioning system (GPS), or wide-area wireless interface (e.g., WiMAX or 3GPP Long-Term Evolution (LTE)). However, other forms of physical layer interfaces and other types of standard or proprietary communication protocols may be used over communication interface 202. Furthermore, communication interface 202 may comprise multiple physical communication interfaces (e.g., a Wifi interface, a BLUETOOTH® interface, and a wide-area wireless interface).

User interface 204 may function to allow computing device 200 to interact with a human or non-human user, such as to receive input from a user and to provide output to the user. Thus, user interface 204 may include input components such as a keypad, keyboard, touch-sensitive or presence-sensitive panel, computer mouse, trackball, joystick, microphone, and so on. User interface 204 may also include one or more output components such as a display screen which, for example, may be combined with a presence-sensitive panel. The display screen may be based on CRT, LCD, and/or LED technologies, or other technologies now known or later developed. User interface 204 may also be configured to generate audible output(s), via a speaker, speaker jack, audio output port, audio output device, earphones, and/or other similar devices.

In some embodiments, user interface 204 may include a display that serves as a viewfinder for still camera and/or video camera functions supported by computing device 200. Additionally, user interface 204 may include one or more buttons, switches, knobs, and/or dials that facilitate the configuration and focusing of a camera function and the capturing of images (e.g., capturing a picture). It may be possible that some or all of these buttons, switches, knobs, and/or dials are implemented as functions on a presence-sensitive panel.

Processor 206 may comprise one or more general purpose processors—e.g., microprocessors—and/or one or more special purpose processors—e.g., digital signal processors (DSPs), graphics processing units (GPUs), floating point units (FPUs), network processors, or application-specific integrated circuits (ASICs). In some instances, special purpose processors may be capable of image processing, image alignment, and merging images, among other possibilities.

Data storage 208 may include one or more volatile and/or non-volatile storage components, such as magnetic, optical, flash, or organic storage, and may be integrated in whole or in part with processor 206. Data storage 208 may include removable and/or non-removable components.

Processor 206 may be capable of executing program instructions 218 (e.g., compiled or non-compiled program logic and/or machine code) stored in data storage 208 to carry out the various functions described herein. Therefore, data storage 208 may include a non-transitory computer-readable medium, having stored thereon program instructions that, upon execution by computing device 200, cause computing device 200 to carry out any of the methods, processes, or functions disclosed in this specification and/or the accompanying drawings. The execution of program instructions 218 by processor 206 may result in processor 206 using data 212.

By way of example, program instructions 218 may include an operating system 222 (e.g., an operating system kernel, device driver(s), and/or other modules) and one or more application programs 220 (e.g., camera functions, address book, email, web browsing, social networking, and/or gaming applications) installed on computing device 200. Similarly, data 212 may include operating system data 216 and application data 214. Operating system data 216 may be accessible primarily to operating system 222, and application data 214 may be accessible primarily to one or more of application programs 220. Application data 214 may be arranged in a file system that is visible to or hidden from a user of computing device 200.

Application programs 220 may communicate with operating system 222 through one or more application programming interfaces (APIs). These APIs may facilitate, for instance, application programs 220 reading and/or writing application data 214, transmitting or receiving information via communication interface 202, receiving and/or displaying information on user interface 204, and so on.

In some vernaculars, application programs 220 may be referred to as "apps" for short. Additionally, application programs 220 may be downloadable to computing device 200 through one or more online application stores or application markets. However, application programs can also be installed on computing device 200 in other ways, such as via a web browser or through a physical interface (e.g., a USB port) on computing device 200.

Camera components 224 may include, but are not limited to, an aperture, shutter, recording surface (e.g., photographic film and/or an image sensor), lens, and/or shutter button. Camera components 224 may be controlled at least in part by software executed by processor 206.

Captured digital images may be represented as a one-dimensional, two-dimensional, or multi-dimensional array of pixels. Each pixel may be represented by one or more values that may encode the respective pixel's color and/or brightness. For example, one possible encoding uses the YCbCr color model. In this color model, the Y channel may represent the brightness of a pixel, and the Cb and Cr channels may represent the blue chrominance and red chrominance, respectively, of the pixel. For instance, each of these channels may take values from 0 to 255 (i.e., the tonal range that a single 8-bit byte can offer). Thus, the brightness of a pixel may be represented by a 0 or a value near zero if the pixel is black or close to black, and by a 255 or a value near 255 if the pixel is white or close to white. However, the value of 255 is a non-limiting reference point, and some implementations may use different maximum values (e.g., 1023, 4095, etc.).

Nonetheless, the YCbCr color model is just one possible color model, and other color models such as a red-green-blue (RGB) color model or a cyan-magenta-yellow-key (CMYK) may be employed with the embodiments herein. Further, the pixels in an image may be represented in various file formats, including raw (uncompressed) formats, or compressed formats such as Joint Photographic Experts Group (JPEG), Portable Network Graphics (PNG), Graphics Interchange Format (GIF), and so on.

Some pixel encodings—including the YCbCr color model—use 8 bits to represent the brightness of each pixel. Doing so is referred to as LDR imaging. As a result, only 256 levels of brightness may be supported. However, real-world scenes often exhibit a wider dynamic range of brightness than can be reasonably represented by LDR imaging. For example, a scene of an individual standing in a dark room in front of a window may include both extremely bright regions and extremely dark regions. However, use of LDR imaging to capture an image of such a scene may result in loss of detail in the bright region and/or the dark region based on the TET with which the image was captured.

A short TET may result in a reasonably accurate representation of the bright regions of a scene, but underexposure of the dark regions. Conversely, a long TET may result in a reasonably accurate representation of the dark regions, but may overexpose the bright regions. In the example scene introduced above, if the TET is too long, the features in the room may appear properly-exposed, but the features outside the window may appear whitewashed. But if the TET is too short, the features outside the window may appear normal but the features in the room may appear darkened. Either of these outcomes is undesirable. For some scenes, there may not be a single TET that results in a captured image representing the details in both bright regions and dark regions with acceptable detail.

Camera devices may support an auto-exposure (AE) mode in which, prior to output image capture, the camera determines the TET based on the brightness of the scene. For example, the user may observe the scene in the camera's viewfinder before triggering image capture. During this period, the camera may make an initial estimate of the proper TET, capture a preview image with that TET, and then evaluate the pixels in the captured image. Then, as one possible implementation, if a majority (or some other sufficient fraction) of the pixels in the preview image are over-exposed, the camera may decrease the TET and capture another preview image. If a majority (or some other sufficient fraction) of the pixels in this preview image are under-exposed, the camera may increase the TET and capture yet another preview image.

For instance, if the majority of the pixels in the captured image exhibit a brightness value above a high threshold level (e.g., 240), the camera may decrease the TET. On the other hand, if a majority of the pixels exhibit a brightness level below a low threshold level (e.g., 96), the camera may increase the TET.

Alternatively or additionally, a target average pixel value for some or all of the scene's pixels may be determined. If the actual average pixel value is above the target average pixel value, the TET may be decreased, and if the actual average pixel value is below the target average pixel value, the TET may be increased. The target average pixel value can also be tuned differently depending on how much contrast there is in the scene. For example, in a low-contrast scene, the target average pixel value may be bright (e.g., 200). But in a high-contrast scene, the target average pixel value may be lower (e.g., 128).

This process may continue until the camera determines that an image should be captured and stored (e.g., the user activates the shutter button). During this process, if the characteristics of the scene are relatively unchanging, the camera usually converges on an estimated "best" TET based on the brightness of the scene. In some embodiments, the image displayed on the camera's viewfinder may omit information from one or more of the captured preview images or combine information from two or more of the captured preview images.

In some cases, the camera might not treat all pixels equally when determining an "average" brightness of the scene. Using a technique described as "center-weighted averaging," pixels near the middle of the scene may be considered to be more important. Thus, these pixels may be weighted more than pixels illustrating other areas of the scene. Alternatively, pixels in other locations of an image may be given more weight. For instance, if the camera detects a human face (or some other object of interest) in a particular location other than the center of the image, the camera may give a higher weight to the associated pixels.

In this way, AE algorithms may seek to determine a TET that produces a large number (e.g., the largest number) of properly-exposed pixels. However, given the range limitations of LDR imaging, even images captured in AE mode may contain portions that are whitewashed or darkened. Thus, as noted above, some scenes there may be no single "best" TET.

AE algorithms may differ from the description above. For instance, some may be more complex, treating different colors differently, considering the spatial and/or structural components of a scene, and/or measuring contrast between regions. The embodiments herein, however, may operate with any AE algorithm now known or developed in the future.

High dynamic range (HDR) imaging has been proposed as a way of compensating for the deficiencies of LDR imaging. In a possible implementation, HDR imaging may involve a camera capturing multiple images of a scene at various TETs, and then digitally processing these captured images to make a single image that contains a reasonable representation of the details in most or all regions of the scene, including those that are very bright and very dark. However, determining TETs for capturing images can be problematic. In particular, difficulty in adjusting TETs for a particular scene has created limitations in HDR imaging. The methods and implementations described herein may provide computational efficiency, robustness to artifacts, and/or enhanced image quality.

In the following, the term "LDR image" may refer to an image captured using LDR imaging, and the term "LDR scene" may refer to a scene that has been determined to be reasonably represented using LDR imaging. Similarly, the term "HDR image" may refer to an image captured using HDR imaging, and the term "HDR scene" may refer to a scene that has been determined to be reasonably represented using HDR imaging. Furthermore, the term "LDR imaging" may be used interchangeably with the term "LDR image acquisition," and the term "HDR imaging" may be used interchangeably with the term "HDR image acquisition."

Figure 3:
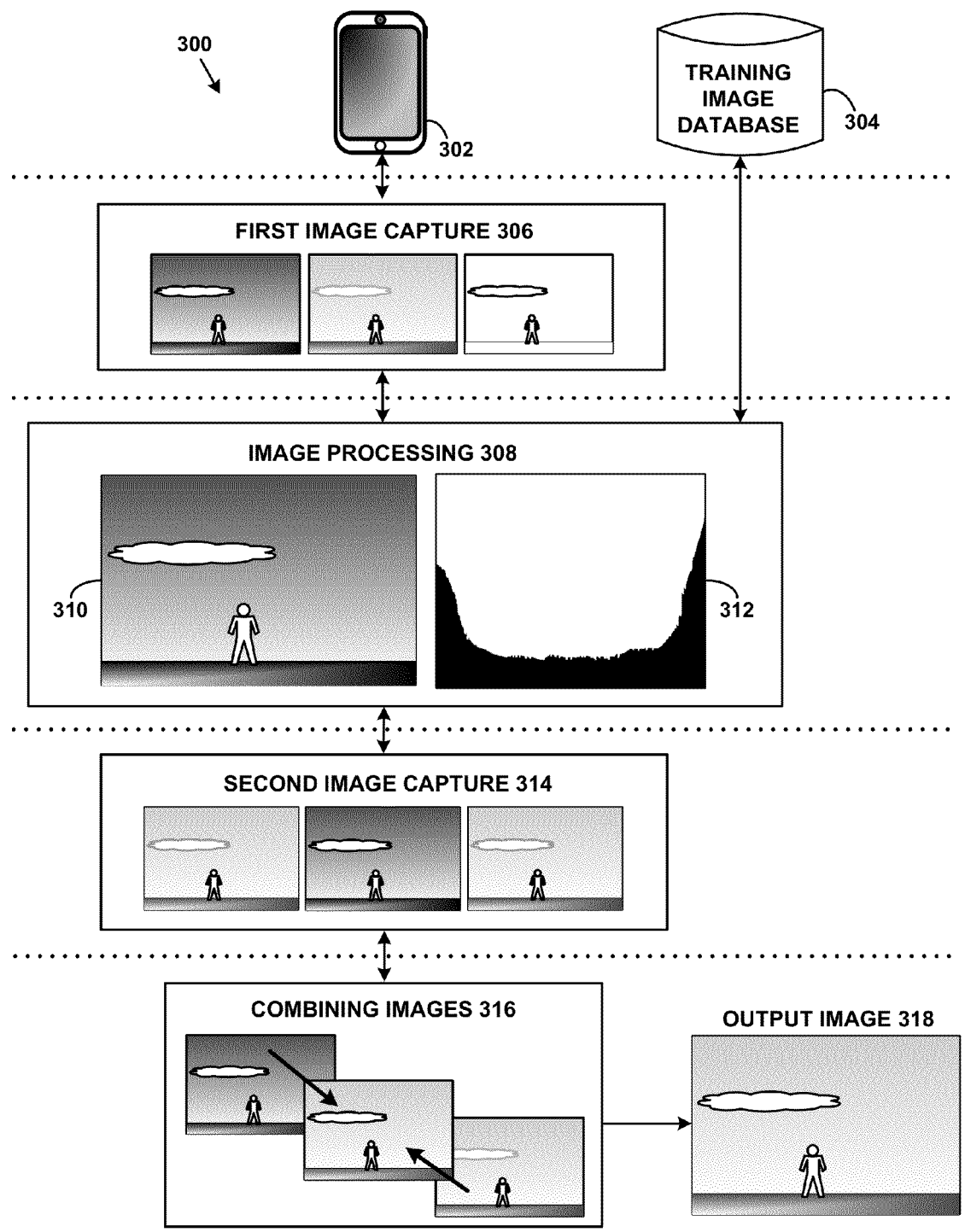
FIG. 3 depicts a flow chart, in accordance with an example embodiment.

FIG. 3 depicts a flow chart, in accordance with an example embodiment. At a high level, flow chart 300 represents an imaging pipeline for a digital camera device 302. For instance, flow chart 300 may represent a number of steps performed by digital camera device 302 to determine whether to use LDR or HDR image acquisition for a particular scene, determine one or more TETs with which to capture images of the scene, and whether and/or how to combine the captured images into an output image that is a reasonably satisfactory representation of the scene. In this way, digital camera device 302 can dynamically adapt to the lighting pattern of the scene, whether that pattern is dark, bright, or some combination of both. Digital camera device 302 may have the same or similar capabilities as digital camera device 100 in FIG. 1.

Flow chart 300 may represent a series of steps performed by digital camera device 302 when a shutter button is triggered. Alternatively or additionally, flow chart 300 may represent steps that are continuously performed when a viewfinder of digital camera device 302 is displaying a representation of a scene. Thus, in some embodiments, the features of flow chart 300 may be performed in a way that is not apparent to the user. For instance, the user may trigger the shutter once, with the intention of capturing a single image. However, digital camera device 302 may capture multiple images in each of first image capture 306 and second image capture 314, and provide an output image 318 that is a combination of one or more images captured during second image capture 314.

It should be noted that not all steps depicted in FIG. 3 need be performed by digital camera device 302. Some steps, such as image processing 308 and combining images 316, for example, could be performed by a different device. For instance, representations of one or more images captured during first image captures 306 and second image capture 314 could be transmitted from a capturing device to a remote computing device. The remote computing device could them perform image processing 308 and combining images 316, possibly transmitting some or all of the results thereof to the capturing device.

Additionally, training image database 304 may be included in digital camera device 302 or alternatively, training image database 304 may be part of a separate device or system that may be accessed by digital camera device 302. In some embodiments, training image database 304 may include representations of training images that can be used to help determine the structure of a payload burst used in second image capture 314.

In first image capture 306, a first group of images of a scene may be captured using a "metering burst sweep." In a metering burst sweep, each image in the group may be captured with a different TET. In some instances, the metering burst sweep may capture consecutive images across a range of TETs (e.g., 1-300 milliseconds, 0.1-500 milliseconds, or some other range). Using such ranges of TETs, the metering burst sweep may capture a series of images with TETs designed to cover this range according to a linear, logarithmic, and/or exponential distribution of TETs, among other possibilities.

As an example, FIG. 3 depicts first image capture 306 including three digital images of a scene, each captured with a different TET. The three images exhibit diverse levels of brightness due to the different TETs used to capture the images. In other examples, more or fewer images may be captured during first image capture 306. These captured images may provide parameters for digital camera device 302 to use when capturing subsequent images of the scene.

The metering burst sweep can be used to determine the characteristics of the scene so that a subsequent payload burst structure for second image capture 314 can be selected. Therefore, in step 308, the images captured at step 306 may be processed. Particularly, step 308 may include merging one or more of the images captured at step 306 in a combined image 310. Step 308 may also include forming a histogram 312 from the merged images, and then using the histogram, and possibly some or all of the information in training image data 304, to classify the scene (e.g., as an LDR scene or an HDR scene), determine the structure of the payload burst based on the classification of the scene, and determine the TETs to use when capturing images according to the payload burst. In some embodiments, the captured images, shown as a result of first image capture 306, may be downsampled prior to merging. Further, the histogram may be an LDR histogram, HDR histogram, an log HDR histogram, or some other form of histogram.

Figure 4A:
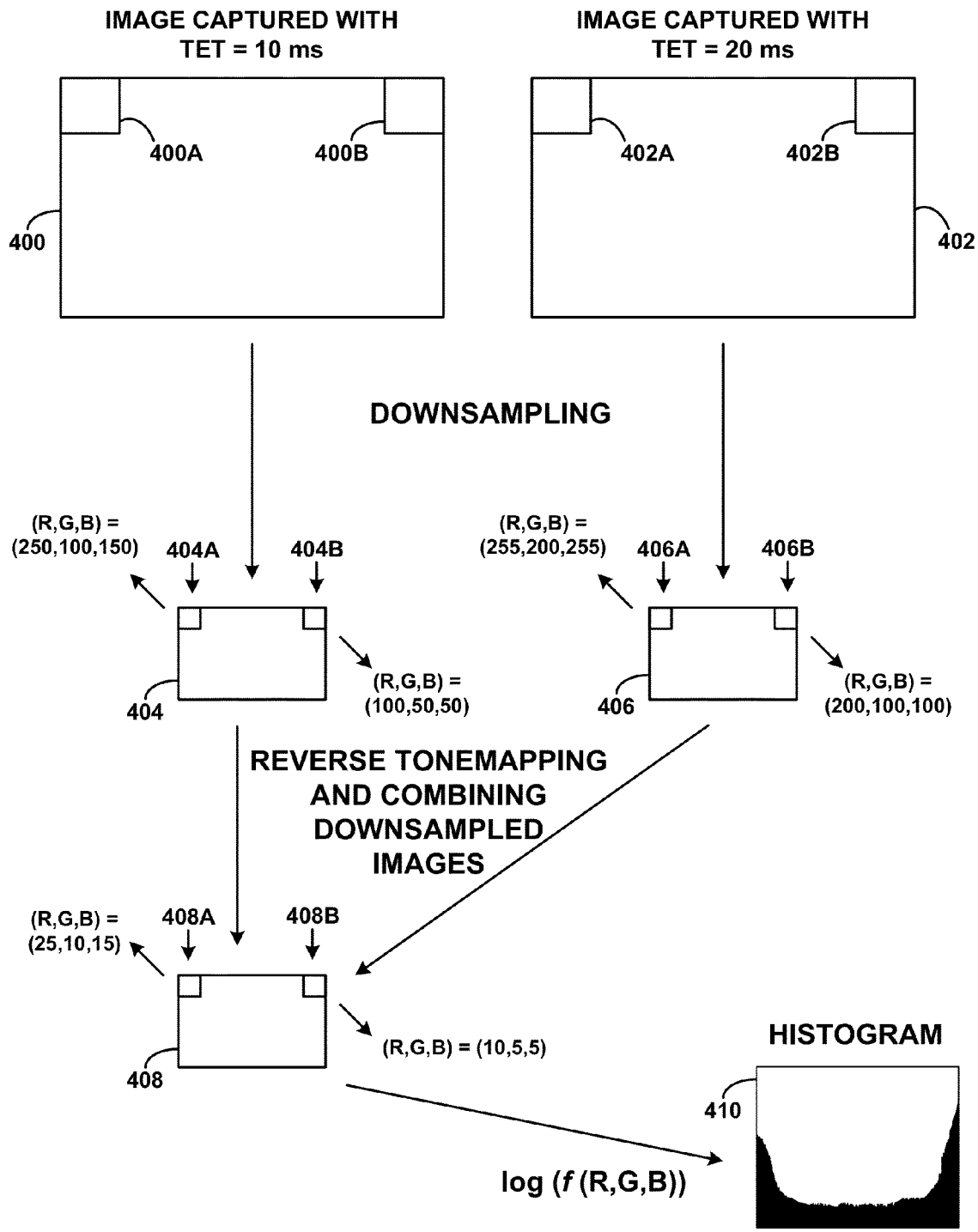
FIG. 4A depicts creating a histogram from one or more captured images, in accordance with an example embodiment.

An example of this process is illustrated in FIG. 4A. For sake of simplicity, assume that the metering burst sweep consist of two images, image 400 and image 402. In practice, anywhere from one to eight or more images may be captured in the metering burst sweep. Image 400 was captured with a TET of 10 milliseconds, while image 402 was captured with a TET of 20 milliseconds. Thus, the pixels of image 402 might be expected to be about twice as bright as those of image 400. In some cases, the pixels in each of images 400 and 402 may be tonemapped. Therefore, the tonemapping process may be reverse for these images. After the tonemapping process is reversed, the pixels of image 402 may be about twice as bright as those of image 400. Tonemapping and reverse tonemapping are discussed in more detail below.

Images 400 and 402 may be downsampled to form images 404 and 406 respectively. Downsampling can be implemented by, for example, dividing a given image into i×j pixel blocks (i and j may take on the same value or different values), and replacing each of these blocks by a single pixel. The value of this replacement pixel can be based on the values of the pixels in the respective i×j pixel block. For instance, the value of the replacement pixel may be determined by taking an average of the values of the pixels in the block, resulting in a "fuzzier," lower-resolution, and smaller downsampled image. Thus, as one possible example, if a 1600×1200 pixel image is divided into 2×2 pixel blocks and downsampled one level, the result is an 800×600 pixel image. If the 1600×1200 pixel image is downsampled two levels (or if the 800×600 pixel image is downsampled one more level), the result is a 400× 300 pixel image, and so on. Nonetheless, a tile can be downsampled in other ways. For example, a 4×4, an 8×8 pixel block or a 16×16 pixel block can be replaced by a single pixel, and more than just one or two levels of downsampling can be performed.

In some embodiments, multiple levels of downsampling may be performed for each image, thus creating a "pyramid" of downsampled images. By using images with multiple levels of downsampling, information regarding both the distribution of light levels in the image and the spatial structure of these light levels may be preserved.

Thus, for instance, FIG. 4A depicts image 400 having pixel block 400A in its top, left corner and pixel block 400B in its top right corner. Additionally, image 402 has pixel block 402A in its top, left corner and pixel block 402B in its top right corner. Each pixel block in each image is downsampled to an individual respective pixel in images 404 and 406— pixel 404A represents a downsampling of pixel block 400A, pixel 404B represents a downsampling of pixel block 400B, pixel 406A represents a downsampling of pixel block 402A, and pixel 406B represents a downsampling of pixel block 402B.

In some cases, an i×j pixel block and its associated downsampled pixel may both be referred to as a "paxel." Thus, pixel block 402A and pixel 404A may both be referred to as a paxel.

For each location in the downsampled images (e.g., pixels 404A and 406A would be considered to be in the same location), the pixel with the highest value less than 255 may be selected. In some embodiments, the pixel value of each color channel in the pixel may be compared to 255. If all of these pixel values are below 255, then the pixel is a candidate for selection. Out of all of the candidate pixels, the one with the highest pixel value may be selected. In other embodiments, a threshold different from 255 (e.g., 250, 245, or a value higher than 255) may be used instead.

FIG. 4A illustrates an example of this process. In downsampled image 404, pixel 404A may have red, green, and blue (R, G, B) values of 250, 100, and 150, respectively. In downsampled image 406, pixel 406A may have (R, G, B) values of 255, 200, and 255, respectively. Since the (R, G, B) values of pixel 404A are all less than 255 but some of the (R, G, B) values of pixel 406A are at 255, pixel 404A is selected. Similarly, pixel 404B may have (R, G, B) values of 100, 50, and 50, respectively, while pixel 406B may have (R, G, B) values of 200, 100, and 100, respectively. Since the (R, G, B) values of pixel 406B are all less than 255, but greater than the (R, G, B) values of pixel 404B, pixel 406B is selected. Other types of comparisons may be used also or instead of the process illustrated in FIG. 4A. For instance, the average of the (R, G, B) values of the respective pixels may be compared. Alternatively, the luma (Y) value of the pixel in the YCbCr color space may be used to test against the threshold.

Each selected pixel may be placed in its respective location in combined image 408. Thus, for instance, pixel 404A may be placed as pixel 408A, and pixel 406B may be placed as pixel 408B in combined image 408. Additionally, the pixels selected for combined image 408 may be reverse tonemapped.

Tonemapping is a set of procedures that include mapping the pixel values according to a pre-determined function. Thus, for instance, some camera devices map pixel values from a linear space (wherein an increase or decrease of k units in pixel value represents a proportional increase or decrease in brightness) to a non-linear space. Tonemapping may be automatically performed for artistic purposes, such as brightening mid-range pixel values. Regardless, in order to reverse tonemap the selected pixels back to linear space, the inverse of the tonemapping function may be applied to the respective pixel values.

Additionally, the pixel values may be divided by the respective TET with which the pixels were captured. Doing so may normalize the pixel values that were captured using the various TETs to a particular range. Thus, for pixel 408A, the (R, G, B) values may be 25, 10, 15, while for pixel 408B, the (R, G, B) values may be 10, 5, 5. On the other hand, for TETs under 1 millisecond (e.g., TETs of 0.25 milliseconds, 0.5 milliseconds, and so on) dividing by the TET may increase the pixel values in combined image 408. In some cases, this may result in these pixel values being greater than 255, and therefore combined image 408 may be an HDR representation of the scene.

Further, a histogram 410 may be created from combined image 408. While there are many ways in which the histogram can be formed, some embodiments may include evaluating a function of the color channels of each pixel. This function may be a maximum or some other function, for instance.

Moreover, the logarithm of this function's output may also be taken, and the resulting value plotted on histogram 410. The distribution of light levels in the real world is logarithmic. Thus, by using a log scale, there is a roughly uniform coverage of that range. For histograms based on linear light levels, more histogram bins might be used. Further, in some embodiments, a weight may be applied to the logarithm of the function's output before placing this output in histogram 410. For instance, a center-weighted average technique may be used to apply a higher weight for pixels that are closer to the center of the captured image, and a lower weight might for pixels that are further from the center of the image.

Regardless, histogram 410 may represent the distribution of pixel values in combined image 408. The vertical axis of the histogram may indicate the number of pixels of each pixel value and the horizontal axis may represent the range of pixel values. The pixel values may be within the range 0-255, or some other range may be used. For instance, an HDR histogram may include pixel values above 255. In some embodiments, an HDR histogram may represent 15-bit pixel values, i.e., from 0 to 32,767. Thus, the log values appearing in the HDR histogram may be in the range of 0 to log(32,767)=4.52.

As an example, histogram 410 plots most of the pixels on the extreme ends of its horizontal axis. This indicated that most of histogram 410 plots image 408 is a shade of black or white. However, since histogram 410 also plots data points in the middle of the horizontal axis, combined image may contain pixels with mid-range brightness as well.

Figure 4B:
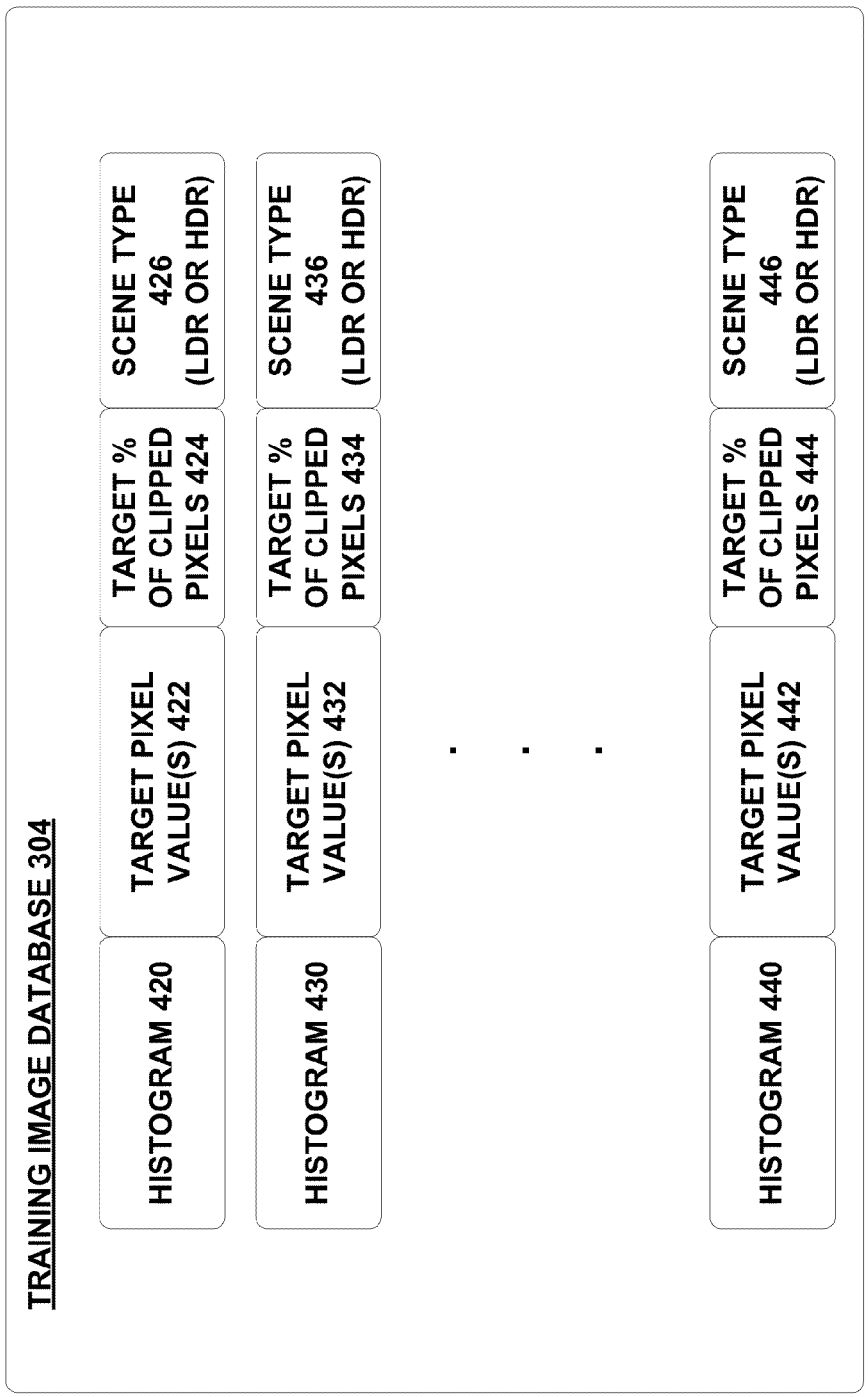
FIG. 4B depicts a training image database, in accordance with an example embodiment.

Still as part of image processing 308, histogram 410 may be compared to one or more histograms of images in training image database 304. As depicted in FIG. 4B, training image database 304 may contain a set of histograms of reference scenes, and/or associated parameters. The histograms of the reference scenes may be HDR histograms, as described above.

FIG. 4B shows training image database 304 containing an entry for histogram 420, target pixel value(s) 422, target percentage of clipped pixels 424, and scene type 426. Histogram 420 may have been derived from one or more images in the same or a similar fashion as described in the context of FIG. 4A, above. Thus, one or more images of a reference scene may be captured using various TETs, and these images may be downsampled and combined into a single image from which histogram 420 is derived. In general, the reference scene from which histogram 420 is derived need not be the same scene from which histogram 410 is derived.

In some embodiments, the percentage of pixels clipped (e.g., pixels having a pixel value of 255 or higher) in the downsampled, combined single image may be stored in target percentage of clipped pixels 424. Clipping may occur when the TET used to capture the image was either too high or too low, and some very dark or very bright details of the scene were lost in the image capture process. In some cases, only pixels clipped at one end of the range may be included in the percentage of pixels clipped. For instance, the percentage of pixels clipped may include only pixels with a pixel value of 255 or higher, and the average pixel value of unclipped pixels may be calculated over all other pixels (e.g., all pixels with a pixel value of 0-254).

Further, an indication of whether the scene was LDR or HDR may be stored in scene type 426. In some implementations, scene type 426 may take on a value of zero when the scene type is LDR, and a value of one when the scene type is HDR. Alternatively, scene type 426 may be within a range, e.g., from 0 to 1. In this case, a value less than a threshold (e.g., 0.5) might indicate an LDR scene type, and any number greater than or equal to the threshold value might indicate an HDR scene type.

Target pixel value(s) 422 may be one or more pixel values that have been determined to be desirable for the associated scene. If the scene is LDR, target pixel value(s) 422 may include a single pixel value, or a range of pixel value(s). This single pixel value (or range) may have been selected so that images of the scene with an average pixel value matching the target pixel value would be reasonably well-exposed. Thus, the target pixel value(s) 422 may be a target average pixel value. Additionally, the target pixel value(s) 422 may be LDR values (e.g., from 0 to 255).

If the scene is HDR, target pixel value(s) 422 may include a short exposure target pixel value (or range), a long exposure target pixel value (or range), and possibly a fallback exposure target pixel value (or range). These pixel values or ranges may have been selected so that HDR images with the short exposure target pixel value for the short exposures and long exposure target pixel value for the long exposures may be reasonable well exposed. The fallback target pixel value may be used if HDR imaging fails (e.g., as discussed below) and a single TET is used to capture the HDR scene.

In some cases, target pixel value(s) 422, target percentage of clipped pixels 424, and scene type 426 may be determined manually by examining several synthetic exposures of the captured images and selecting the pixel value(s) and/or range(s) that appear most pleasing to the eye. Alternatively, target pixel value(s) 422, target percentage of clipped pixels 424, and scene type 426 may be determined algorithmically or automatically.

Training image database 304 may also contain similar entries for histogram 430, target pixel value(s) 432, target percentage of clipped pixels 434, and scene type 436, as well as histogram 440, target pixel value(s) 442, target percentage of clipped pixels 444, and scene type 446. In some embodiments, one or more parameters, such as the target percentage of clipped pixels, may be omitted from training image database 304. Additionally, other parameters may be included in training image database 304. Training image database may store as few as one or several tens, hundreds, or thousands of such entries, each entry possibly relating to a different scene.

As discussed above in the context of an image captured during first image capture 306, multiple levels of downsampling may be performed for each image in training image database 304, thus creating a "pyramid" of downsampled versions of each image. By using images with multiple levels of downsampling, information regarding both the distribution of light levels in the image and the spatial structure of these light levels may be preserved. Histograms for each of these downsampled images may be included in training image data 304.

The information in training image database 304 may be stored therein during calibration, testing, and/or other pre-shipment evaluations before commercial operation, among other possibilities. Alternatively, the information may also be stored on various other devices and systems capable of managing training image database 304. Regardless, the information may be substantially static in nature, though the information may be modified through firmware and/or software updates or other installations.

By comparing histogram 410 (and or a similarly-derived histograms based on downsampled versions of images 400 and 402) with the histograms in training image data 304, the dynamic range of the scene represented in images 400 and 402 may be estimated. This estimated dynamic range may be used to determine, obtain, or otherwise select a payload burst structure for second image capture 314.

For example, each histogram 410 may be compared to each histogram stored in training image data 304. A pair of histograms can be compared in various ways, any of which may be used. In some embodiments, the earth mover's distance (EMD) between the pair of histograms may be calculated. The EMD is 0 when the histograms are identical, and increases with the differences between the histograms. Thus, a lower EMD indicates a good match between the two histograms, and a higher EMD indicates a poor match between the two histograms.

A weight may be derived from the EMD for a particular pair of histograms. For example, the weight may be inversely proportional to its associated EMD value. In some situations, the weight w may be derived as:

$$w = \frac{1}{EMD^n}$$

where EMD is the EMD value and n may be in the range of 1 to 10. However, other values of n may be used. Thus, in some embodiments, the weight may take on a value between 0 and 1. In the case that EMD is 0, and appropriately large weight (e.g., 1) may be chosen. Alternatively, a very small value (e.g., 0.001) may be added to the denominator to avoid dividing by 0. Regardless, a good match between the two histograms may result in a high weight, and a poor match between the two histograms may result in a low weight.

For each pair of histograms (where a first histogram is histogram 410 and a second histogram is from an entry in training image database 304), the weight w may be applied to the respective scene type associated with the second histogram's entry in training image database 304. The result may be averaged over the pairs of histograms to determine an "HDR-ness" of the scene. For instance, if the resulting "HDR-ness" is at or above 0.5 on a scale of 0 to 1, then the scene may be designated for HDR processing, but if the resulting "HDR-ness" is below 0.5 on the same scale, then the scene may be designated for LDR processing.

It should be understood that the embodiment described above is just one possible way of determining the brightness and "HDR-ness" of a scene. Other techniques could be used instead, and some of these other techniques may be based on comparing the parameters (e.g., percentage of clipped pixels and average value of unclipped pixels) of the images captured during first image capture 306 with the same or similar parameters of the images represented in training image database 304. Further techniques may include comparing the respective downsampled image pyramids of the first and second histograms.

In order to determine the TETs for the payload burst, the following example procedure may be used. However, other procedures may be used instead.

For each pair of histograms (again, where the first histogram is histogram 410 and a second histogram is from an entry in training image database 304), the weight w may be applied to the respective target pixel value associated with the second histogram's entry in training image database 304. The result may be averaged to determine a target average pixel value for the scene represented by histogram 410. If the scene type is HDR, two or more target average pixel values may be determined.

For each target average pixel value, interval halving may be used to search for a particular TET value such that if the scene were to be captured with the particular TET value, the resulting image would have the target average pixel value or about the target average pixel value. One possible method for determining a particular TET value based on a target average pixel value is shown in the pseudocode below.

TABLE 1

1.  lo_tet = 0.125 ms
2.  hi_tet = 66.6 * 8 * 4 ms
3.  for (int i = 1; i < t; i++) {
4.      mid_tet = (lo_tet + hi_tet) / 2
5.      pixel_value_at_mid_tet = <synthetically expose the HDR
            Image at 'mid_tet', tonemap it, and extract the
            average pixel value of the resulting LDR image.>

TABLE 1-continued

```
6.      if (pixel_value_at_mid_tet > target_average_pixel_value) {
7.              hi_tet = mid_tet
8.      } else {
9.              lo_tet = mid_tet
10.             }
11.     }
```

At lines 1 and 2 of Table 1, initial low and high TET values (lo_tet and hi_tet, respectively) are defined. These values may be chosen at or near the extreme ends of the range in which the ultimate TET value (mid_tet) is expected to fall. In some embodiments, a broader range or a narrower range may be used.

Lines 3-11 depict a loop that may be iterated t times. The value of t may be selected so that mid_tet converges after t iterations of the loop. In some embodiments t may be as low as 2 or 3, but in other embodiments, t may be 5, 10, 20, 50, 100, or some other value. Nonetheless, at line 4, mid_tet is set to be the average (midpoint) of lo_tet and hi_tet.

At line 5, the pixel value of the image at mid_tet is determined. One possible way of making this determination is to synthetically expose the HDR image as if the image were captured using a TET of mid_tet. The resulting image (which may be an HDR image) may be tonemapped, and the average pixel value of the tonemapped image (pixel_value_at_mid_tet, which may be an LDR value) may be determined.

Synthetic exposure is one way of obtaining an LDR image from an HDR image. Suppose that an HDR image was captured using a TET of T. This HDR image can be synthetically exposed to a TET of p times T by multiplying the pixel values of each pixel in the HDR image by p (p may be greater than or less than one). In the resulting image, all pixel values above 255 are "clipped" to 255. This process simulates the appearance of the scene as if it were captured using a TET of p times T with LDR imaging. Alternatively, a non-log HDR histogram of an HDR image (with or without center-weighted averaging applied) may be used. After this step, whatever processing would normally be applied to the linear image (such as tonemapping) may be emulated, in order to produce a synthetic LDR image. The average value in that image (applying center-weighted averaging if desired) may be taken and compared to the target pixel value.

At lines 6-11, if this resulting average pixel value is greater than the target average pixel value, then mid_tet is too high, and hi_tet is set to be mid_tet in order to reduce mid_tet in the next iteration. On the other hand, if the resulting average pixel value is less than or equal to the target average pixel value, then the mid_tet is too low, and lo_tet is set to be mid_tet in order to increase mid_tet in the next iteration.

The process illustrated by Table 1 may be repeated for each TET value that may be used in the payload burst structure. Thus, if the scene is determined to be an LDR scene, the process of Table 1 may be carried out for one TET. However, if the scene is determined to be an HDR scene, the process of Table 1 may be carried out for two or more TETs (e.g., the short TET, the long TET, and/or the fallback TET), all three of which may have different target average LDR pixel values.

In step 314, the second group of images may be captured. The number of images captured and the arrangement of TETs used to capture these images may be referred to as a "payload burst." For example, in FIG. 3 second image capture 314 includes three images of a scene, each captured with a TET identified in step 308. It should be understood that the TETs identified in step 308 may be the same or different than the TETs used to capture images in step 306. Additionally, it is possible that all three images in second image capture 314 are captured with the same or similar TETs.

In step 316, images from the second group of images may be combined. Combining images may include aligning two or more of the images. In some instances, images may be aligned globally (i.e., aligning whole images as opposed to portions of images), locally (i.e., aligning portions of images), or possibly both globally and locally. Further, combining two or more images may also include merging them to form an output image 318. This merging may be carried out in accordance with any image fusion technique now known or developed in the future.

Merging the images in the second group of images may result in output image 318 being sharper and/or better-exposed than any of the individual images in the second group. For instance, if some of the images in second image capture 314 are captured with the same or similar TETs, these images may be merged to reduce noise in one or more sections of the images. Alternatively or additionally, if the images in second image capture 314 are captured with two or more different TETs, at least some images with different exposure times may be merged according to HDR procedures. Regardless, the output image may be stored on a computer-readable medium and/or displayed on an output medium such as the multi-element display 106 of FIG. 1.

In some embodiments, the arrangements of various possible payload burst structures may be determined based on the TETs determined in step 308, as well as an understanding of combining images step 316. While numerous arrangements of payload burst structures may be possible, three examples are described herein.

TABLE 2

| Scene Type | Payload Burst Structure |
|---|---|
| LDR | T T T T |
| HDR | L S L L S L L S L L |
| HDR (with fallback) | L S L L S L L F F F |

Table 2 illustrates these examples. In the first example, the scene type is LDR. In this example, the payload burst structure includes four images captured sequentially, and may be referred to as an "LDR burst structure." Each "T" in the Payload Burst Structure column of Table 2 may represent a captured image. Each of these images may be captured using the same or a similar TET that was determined in step 308. In some embodiments, fewer or more images may be captured in an LDR payload burst. For example, as few as one, or as many as ten or more images may be included.

Regardless of the number of images captured, some of these images may be aligned and combined in step 316. For instance, if m images are captured in the payload burst, the sharpest one of these images may be selected as a "primary image," and the remaining m−1 images may be considered "secondary images." In some implementations, the sharpness of an image may be measured by the image's resolution and/or boundaries between zones of different tones and/or colors in the image. Alternatively or additionally, other sharpness measurements may be used.

Further, zero or more of the m−1 secondary images may then be aligned and merged with the sharpest image. For instance, alignment may be attempted between each of the secondary images and the sharpest image, respectively. If the alignment fails for parts of a respective secondary image, those parts may be discarded, and not combined with the primary image. In this way, the sharpest image may be denoised with information from some or all of the secondary images.

In the second example, the scene type is HDR. In this example, the payload burst structure includes ten images captured according to a pattern of long and short TETs, and may be referred to as an "HDR burst structure." In the Payload Burst Structure column of Table 2, each "L" may represent an image captured with the long TET, each "S" may represent an image captured with the short TET. Thus, the pattern of "L S L L S L L S L L" may indicate that the first image of the payload burst is captured using the long TET, the second image is captured using the short TET, the third and fourth images are captured using the long TET, the fifth image is captured using the short TET, the sixth and seventh images are captured using the long TET, the eighth image is captured using the short TET, the ninth image is captured using the long TET, and the tenth image is captured using the long TET.

The long and short TETs may be determined based on the results of image processing 308. Thus, the long and short TETs may be selected so that the resulting images captured with these TETs can be combined using HDR procedures. The long TET may be used to capture the details in dark sections of the scene, while the short TET may be used to capture the details in bright sections of the scene.

Examples of short TET values may include TETs of 1 millisecond, 2 milliseconds, and/or 8 milliseconds, while examples of long TET values may include TETs of 20 milliseconds, 40 milliseconds, and/or 80 milliseconds. However, short and long TETs may take on different values.

Despite the payload burst in the second example having a particular structure in Table 1, other structures may be used. For example, payload burst structures of "L S L S L S L S L S" or "L L S L L S L L S L" could potentially provide suitable patterns of long and short TETs. Further, some payload burst structures may include medium TETs (denoted by an "M"). Thus, additional example payload bursts may include "S M L L L S M L L L" or "S M L S M L S M L L" structures.

In some embodiments, a payload burst structure may include more or fewer than ten images. Generally speaking, the determining the length of the payload burst structure involves a tradeoff. On one hand, a long payload burst (i.e., a payload burst with a large number of image captures) is desirable because the likelihood of one or more of the captured image being well-exposed and sharp is increased. On the other hand, if the payload burst is too long, the likelihood of ghosting due to movement in the scene is also increased. Additionally, darker scenes may benefit from images captured using a longer TET, so that more light can reach the recording surface. Therefore, the payload burst structure may be based, possibly in part, on these considerations.

In the third example, the scene type is also HDR. However, in this example, the associated payload burst structure (which also may be referred to as an HDR burst structure) includes seven images captured according to a pattern of long and short TETs, followed by three fallback TETs. Each "F" may represent an image captured with the fallback TET, and the fallback TET may take on a value different from both the long and short TETs.

Regardless of the type of payload burst structure, the images of an HDR scene may be aligned and combined. Images captured using the short TET may be referred to as "short images" for convenience, and images captured with the long TET may be referred to as "long images" for convenience.

In some embodiments, the sharpest short image may be selected, from the short images, as the primary short image. Zero or more of the remaining secondary short images may then be aligned and merged with the primary short image. For instance, alignment may be attempted between each of the secondary short images and the primary short image, respectively. If the alignment fails for parts of the respective secondary short image, those parts may be discarded, and not combined with the primary short image. In this way, the sharpest short image may be denoised with information from some of the secondary short images.

The same or a similar process may be undertaken for the long images. For example, the sharpest long image may be selected, from the long images, as the primary long image. Zero or more of the remaining secondary long images may then be aligned and merged with the primary long image. Alignment may be attempted between each of the secondary long images and the primary long image, respectively. If the alignment fails for parts of the respective secondary long image, those parts may be discarded, and not combined with the primary long image.

The resulting combined short image (e.g., the sharpest short image possibly denoised by information from zero or more secondary short images) and the resulting combined long image (e.g., the sharpest long image possibly denoised by information from zero or more secondary long images) may then be aligned. If the alignment succeeds, these two images (e.g., both LDR images) may be combined according to HDR procedures. For instance, they may be combined into an HDR image, and the HDR image may then be tonemapped so that its brightness falls within a range commensurate with the display abilities of convention video output devices (e.g., pixel values between 0 and 255, inclusive). The resulting tonemapped HDR image may be designated as output image 318. In some embodiments, if the signal-to-noise ratio of part or all of output image 318 is still lower than a threshold value, a de-noising procedure may be applied to further reduce noise. Additionally, output image 318 may also be sharpened, possibly after applying the de-noising procedure. In general, various types of HDR fusion algorithms, such as Exposure Fusion or Local Laplacian Filters, may be used to merge short and long images. If medium TETs are used in the payload burst structure, these HDR fusion algorithms may be applied to one or more medium images as well.

If the alignment fails between the combined short image and the combined long image, then the HDR processing fails. However, if fallback images were captured, one or more of the fallback images may be used to form output image 318. For instance, the sharpest fallback image may be selected. Zero or more of the remaining secondary fallback images may be aligned and combined with the sharpest fallback image carried out in a similar fashion as the processes described above for the short and long images. For payload burst structures without fallback images in which alignment fails, the combined long or short image may be used to form output image 318.

Figure 5:
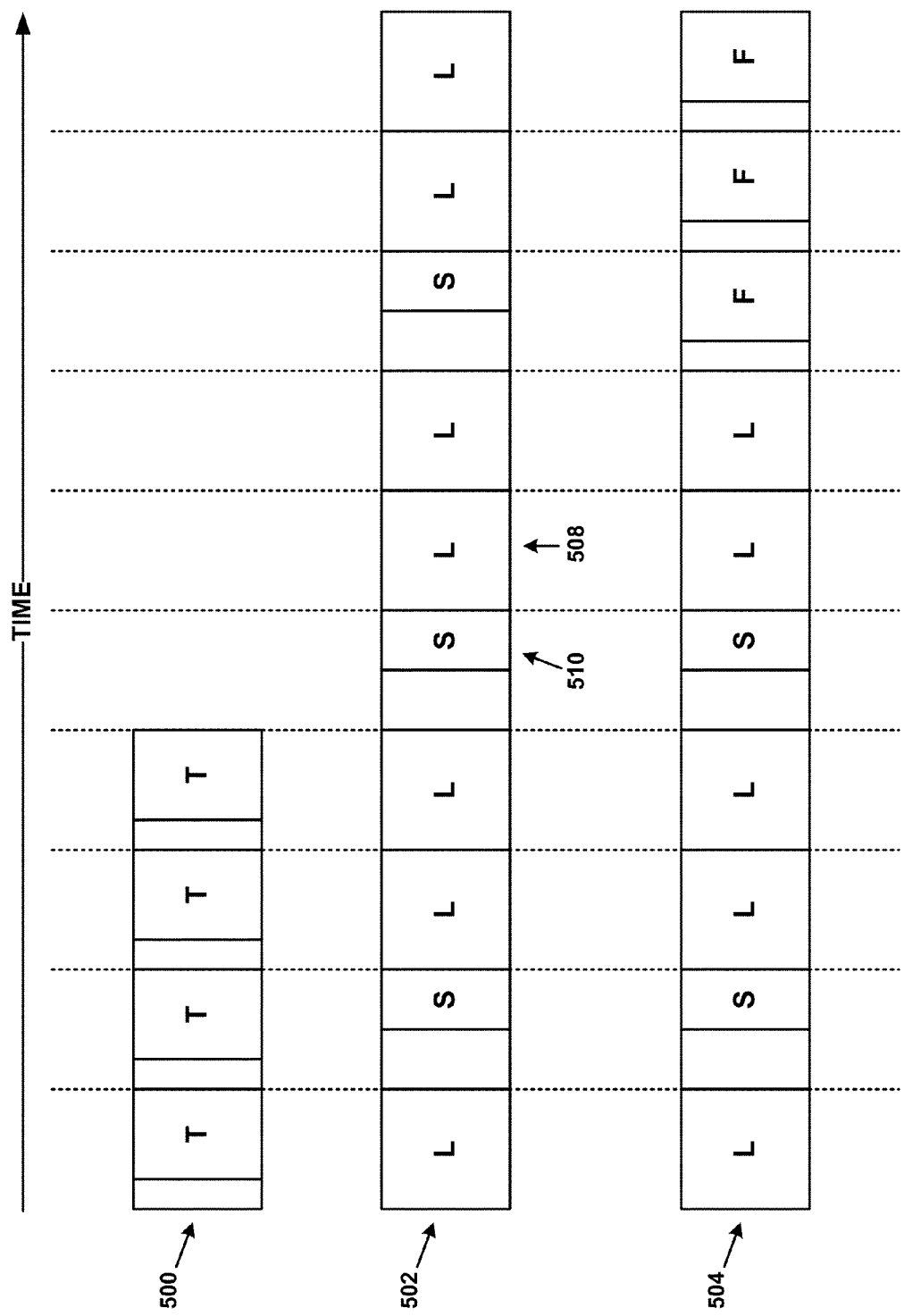
FIG. 5 depicts payload burst structures for capturing images, in accordance with an example embodiment.

Example payload burst structures are further illustrated in FIG. 5. Payload burst structure 500 may represent a payload burst for an LDR scene, payload burst structure 502 may represent a payload burst for an HDR scene, and payload burst structure 504 may represent a payload burst for an HDR scene with fallback. Each burst structure shows the approximate duration of the TET for each image capture. For example, for burst structures 502 and 504, short TETs are of a lesser duration than long TETs, and the duration of fallback TETs are between that of short and long TETs.

In FIG. 5, the vertical dotted lines depict epochs in time at which an image capture can begin. Some electronic image sensors operate at a particular frequency, such as 30 hertz. A sensor operating at this frequency can capture 30 images per second, or approximately one image every 33.33 milliseconds. Thus, the duration between the epochs in FIG. 5 may be 33.33 milliseconds. Nonetheless, for low-light scenes, the exposure time may be longer than 33.33 milliseconds, and the operating frequency of the image sensor may be adjusted downward accordingly. In this example, a TET longer than 30 milliseconds can be achieved by increasing the gain component of the TET.

For some sensors, image capture may be activated only at the end of such an epoch. Thus, as shown in FIG. 5, each image capture ends at the edge of a respective epoch. However, due to their varying TETs, some image captures may begin at different times. Alternatively, for some image sensors, image capture may be activated only at the beginning of an epoch.

It should be understood that various other techniques, procedures, and/or algorithms may be used determine a payload burst structure. Thus, the discussion above accompanying Table 2 and FIG. 5 above merely provides some possible payload burst structures. Other techniques may be used without departing from the scope of the embodiments herein.

For example, in some embodiments, the average pixel value of the tonemapped image (e.g., step 5 in Table 1) may be calculated using either an RMS or SMR method, based on the length of the TET. The RMS average of n values may be calculated as:

$$RMS = \sqrt{\frac{x_1^2 + x_2^2 + \ldots + x_n^2}{n}}$$

The SMR average of n values may be calculated as:

$$SMR = \left(\frac{\sqrt{x_1} + \sqrt{x_2} + \ldots + \sqrt{x_n}}{n}\right)^2$$

For shorter TETs, e.g., the short TETs and/or fallback TETs of an HDR payload burst, or possibly the TETs of an LDR burst, it may be desirable to attempt to increase or maximize the brightness of the pixels without clipping them. Thus, taking the RMS average of the pixel values puts more weight on the brighter pixels. For longer, TETs, e.g., the long TETs of an HDR payload burst, it may be desirable to emphasize the darker parts of the scene. Thus, taking the SMR average of the pixel values puts more weight on the darker pixels.

Another variation is illustrated in the context of burst structure 502 of FIG. 5. This variation involves selecting the sharpest short image. For sake of argument, assume that the sharpest long image is long image 508. Then, instead of selecting the sharpest short image as the primary short image, the short image that was captured closest in time to the sharpest long image may be selected as the primary short image. This could be, for instance, short image 510, which immediately precedes long image 508. Then, the remaining secondary short images may be aligned with and/or combined into (as the alignments permit) the primary short image. Alternatively, if the image sensor captures images at the beginning of the epoch, a short image following (perhaps immediately following) the sharpest long image may be selected as the primary short image. As an alternative, a temporally-adjacent short image/long image pair may be selected so that, together, these images maximize a combined-sharpness metric.

In some embodiments, the payload burst structure may be based on whether the image sensor captures images with an exposure time of less than the readout time of the images sensor's pixels (referred to herein as sub-readout exposure times) at the beginning or end of an image capture epoch. If the image sensor captures sub-readout exposure times at the end of the image capture epoch, the payload burst structure may include one or more two-TET subsequences of a short TET immediately followed by a long TET. If the image sensor captures sub-readout exposure times at the beginning of the image capture epoch, the payload burst structure may include one or more two-TET subsequences of a long TET immediately followed by a short TET.

One possible advantage of selecting the primary long image in this fashion is to reduce motion blur, or "ghosting," effects. For example, if a scene contains motion, merging multiple images captured from the scene may result in the motion appearing in the merged image as a blur. In general, the greater the difference in time between when the images are captured, the greater this blurring. By selecting primary long and short images that are close to one another in time, the ghosting may be reduced It should be noted that the steps illustrated by flow chart 300 may be carried out by various types of cameras and/or computing devices, such as those exemplified by digital camera device 302 and/or computing device 200. Further, it may be possible to distribute aspects of some individual steps between multiple cameras and/or computing devices. For example, first image capture 306 and second image capture 314 may occur on digital camera device 302. Further, image processing 308 and combining images 318 may occur on a different computing device. Other combinations of distributing individual steps may also exist.

Figure 6:
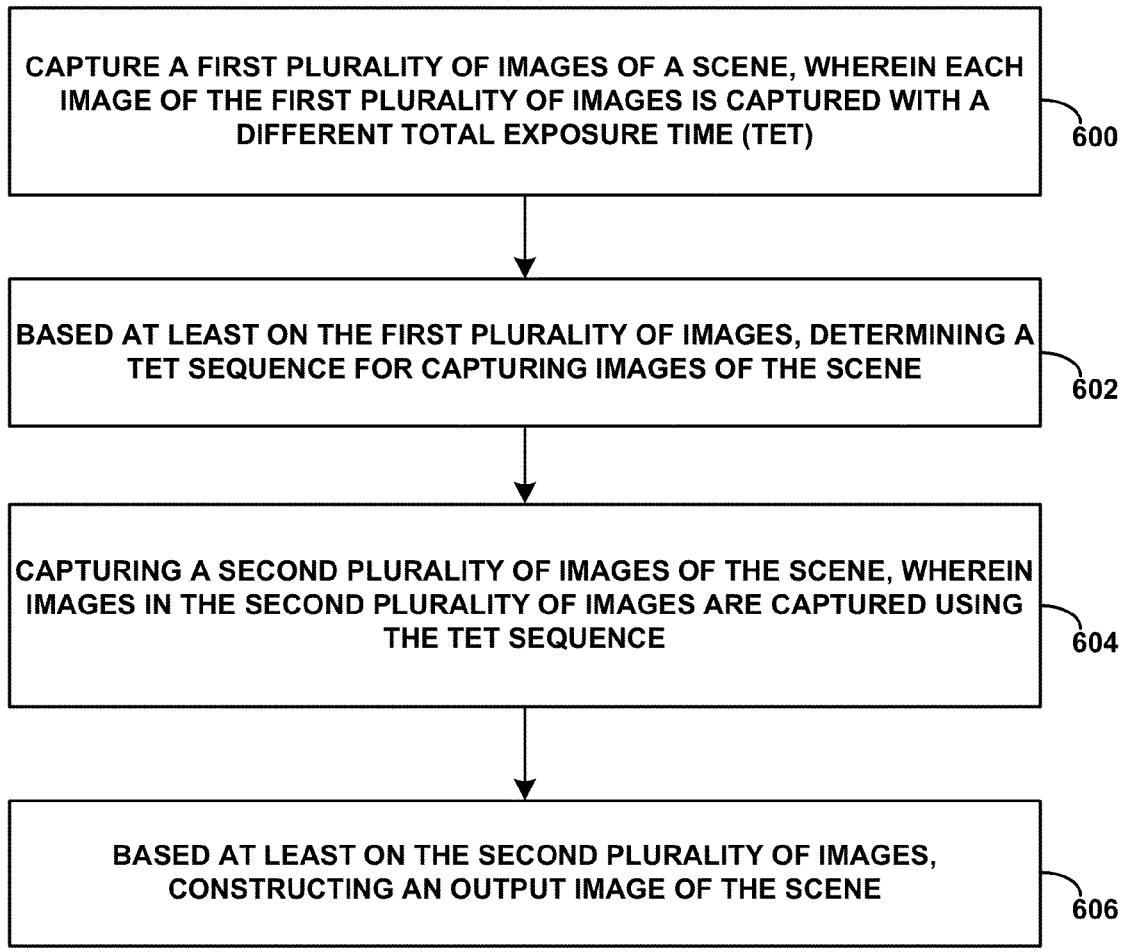
FIG. 6 depicts a flow chart, in accordance with an example embodiment.

FIG. 6 depicts a flow chart, in accordance with an example embodiment. At step 600, a first plurality of images of a scene may be captured, perhaps by an image sensor. Each image of the first plurality of images may be captured with a different total exposure time (TET).

At step 602, based at least on the first plurality of images, a TET sequence for capturing images of the scene may be determined. Determining the TET sequence may involve determining a scene histogram based on at least one of the images in the first plurality of images of the scene. The scene histogram may be based on downsampling and combining the images in the first plurality of images of the scene.

In some embodiments, additional histograms may be stored in a training image database. These histograms may be based on at least two images captured of respective scenes. The histograms may be associated with respective dynamic range parameters, where the respective dynamic range parameters indicate whether the respective scenes are LDR or HDR. Determining the TET sequence may further involve comparing the scene histogram to at least one histogram in the training image database, and based on an outcome of the comparison, determining a dynamic range parameter for the scene from the respective dynamic range parameters, where the TET sequence is further based on the dynamic range parameter for the scene.

If the dynamic range parameter for the scene indicates that the scene is LDR, then determining the TET sequence may involve selecting a single TET value to use in the TET sequence. If the dynamic range parameter for the scene indicates that the scene is HDR, then determining the TET sequence may involve selecting a short TET value and a long TET value to use in the TET sequence. If the scene is HDR, determining the TET sequence may also involve selecting a fallback TET value to use in the TET sequence.

In some embodiments, the histograms in the training database may also be associated with respective target pixel values. In these embodiments, determining the TET sequence may further involve determining one or more target pixel values for the scene based on the respective target pixel values in the training database, selecting one or more TET values to use in the TET sequence based on the one or more determined target pixel values.

At step 604, a second plurality of images of the scene may be captured by the image sensor. The images in the second plurality of images may be captured using the TET sequence. At step 606, based at least on the second plurality of images, an output image of the scene may be constructed.

Determining the TET sequence may involve determining that the scene is an LDR scene and defining a common value for TETs in the TET sequence. Constructing the output image of the scene may involve aligning and combining one or more of the images in the second plurality of images captured using the common value.

Alternatively or additionally, determining the TET sequence may involve determining that the scene is an HDR scene and defining a short TET value and a long TET value. Constructing the output image of the scene may involve aligning and combining (i) one or more of the images in the second plurality of images captured with the short TET value, and (ii) one or more of the images in the second plurality of images captured with the long TET value.

Alternatively or additionally, determining the TET sequence may involve determining that the scene is an HDR scene and defining a short TET value, a long TET value, and a fallback TET value. Constructing the output image of the scene may involve attempting to align (i) one or more of the images in the second plurality of images captured with the short TET value, with (ii) one or more of the images in the second plurality of images captured with the long TET value. Constructing the output image of the scene may further involve determining that alignment of (i) the one or more of the images in the second plurality of images captured with the short TET value, and (ii) the one or more of the images in the second plurality of images captured with the long TET value has failed. Constructing the output image of the scene may also involve, in response to determining that the alignment has failed, aligning and combining one or more of the images in the second plurality of images captured with the fallback TET value to form the output image.

Figure 7:
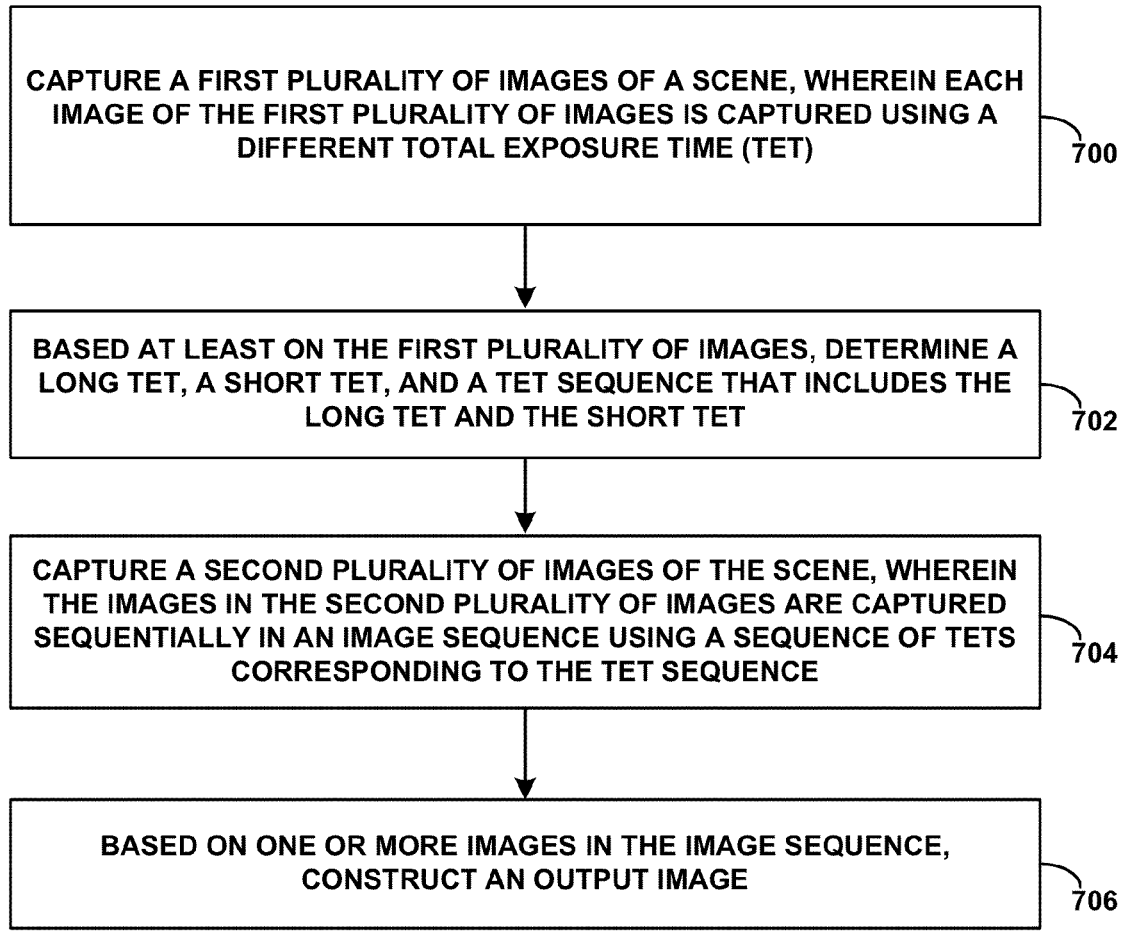
FIG. 7 depicts another flow chart, in accordance with an example embodiment.

FIG. 7 depicts another flow chart, in accordance with an example embodiment. At step 700, a first plurality of images of a scene may be captured by an image sensor. Each image of the first plurality of images may be captured using a different total exposure time (TET). At step 702, based at least on the first plurality of images, a long TET, a short TET, and a TET sequence that includes the long TET and the short TET may be determined.

At step 704, a second plurality of images of the scene may be captured by the image sensor, wherein the images in the second plurality of images are captured sequentially in an image sequence using a sequence of TETs corresponding to the TET sequence. The image sequence may include a three-image sub-sequence of a first long-TET image captured using the long TET, followed by a short-TET image captured using the short TET, followed by a second long-TET image captured using the long TET. Alternatively, the image sequence may include a three-image sub-sequence of a first long-TET image captured using the long TET, followed by a second long-TET image captured using the long TET, followed by a short-TET image captured using the short TET. The pattern in the subsequence may be chosen based on characteristics of the camera device (e.g., whether a rolling shutter is used and/or other image sensor characteristics) and/or characteristics of the scene (e.g., average pixel value or some other metric). Regardless, the sub-sequence may repeat one or more times through the payload burst structure.

At step 706, based on one or more images in the image sequence, an output image may be constructed. In some embodiments, the image sequence may include a two-image sub-sequence of a primary short-TET image followed by a primary long-TET image. The image sequence may also include one or more secondary short-TET images and one or more secondary long-TET images. The primary short-TET image and the secondary short-TET images may be captured using the short TET, and the primary long-TET image and the secondary long-TET images may be captured using the long TET. Constructing the output image may involve forming a combined short-TET image, where the combined short-TET image includes the primary short-TET image and at least part of the one or more secondary short-TET images, forming a combined long-TET image, where the combined long-TET image includes the primary long-TET image and at least part of the one or more secondary long-TET images, and forming the output image, where the output image includes at least part of the combined short-TET image and at least part of the combined long-TET image.

Alternatively or additionally, the image sequence may include a long-TET image captured using the long TET. Constructing the output image may involve determining that the long-TET image is a sharpest image of all images in the image sequence captured using the long TET. Based on the long-TET image being the sharpest image of all images in the image sequence captured using the long TET, selecting the long-TET image as a primary long-TET image, and selecting, as a primary short-TET image, an image captured using the short TET that is adjacent to the primary long-TET image in the image sequence. Constructing the output image may further involve forming a combined short-TET image, where the combined short-TET image includes the primary short-TET image and at least part of one or more images from the image sequence that were captured using the short TET, forming a combined long-TET image, where the combined long-TET image includes the primary long-TET image and at least part of one or more images from the image sequence that were captured using the long TET, and forming the output image, where the output image includes at least part of the combined short-TET image and at least part of the combined long-TET image.

In some examples, the primary short-TET image may immediately precede the primary long-TET image in the image sequence. The short-TET image that immediately precedes the primary long-TET image in the image sequence may be selected as the primary short-TET image based on image capture ending at the edge of respective image capture epochs.

In other examples, the primary short-TET image may immediately follow the primary long-TET image in the image sequence. The short-TET image that immediately follows the primary long-TET image in the image sequence may be selected as the primary short-TET image based on image capture beginning at the edge of respective image capture epochs.

The steps depicted in FIGS. 6 and 7 may be carried out by a camera device, such as digital camera device 100, a computing device, such as computing device 200, and/or by two or more distinct devices. For instance, in some embodiments, the image capture steps may be performed by an image sensor and the remaining steps may be performed by a separate computing device. Other arrangements are possible. Further, the flow charts depicted in FIGS. 6 and/or 7 may be modified according to the variations disclosed in this specification and/or the accompanying drawings.

The above detailed description describes various features and functions of the disclosed systems, devices, and methods with reference to the accompanying figures. In the figures, similar symbols typically identify similar components, unless context indicates otherwise. The illustrative embodiments described in the detailed description, figures, and claims are not meant to be limiting. Other embodiments can be utilized, and other changes can be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

With respect to any or all of the message flow diagrams, scenarios, and flow charts in the figures and as discussed herein, each step, block and/or communication may represent a processing of information and/or a transmission of information in accordance with example embodiments. Alternative embodiments are included within the scope of these example embodiments. In these alternative embodiments, for example, functions described as steps, blocks, transmissions, communications, requests, responses, and/or messages may be executed out of order from that shown or discussed, including in substantially concurrent or in reverse order, depending on the functionality involved. Further, more or fewer steps, blocks and/or functions may be used with any of the message flow diagrams, scenarios, and flow charts discussed herein, and these message flow diagrams, scenarios, and flow charts may be combined with one another, in part or in whole.

A step or block that represents a processing of information may correspond to circuitry that can be configured to perform the specific logical functions of a herein-described method or technique. Alternatively or additionally, a step or block that represents a processing of information may correspond to a module, a segment, or a portion of program code (including related data). The program code may include one or more instructions executable by a processor for implementing specific logical functions or actions in the method or technique. The program code and/or related data may be stored on any type of computer-readable medium, such as a storage device, including a disk drive, a hard drive, or other storage media.

The computer-readable medium may also include non-transitory computer-readable media such as computer-readable media that stores data for short periods of time like register memory, processor cache, and/or random access memory (RAM). The computer-readable media may also include non-transitory computer-readable media that stores program code and/or data for longer periods of time, such as secondary or persistent long term storage, like read only memory (ROM), optical or magnetic disks, and/or compact-disc read only memory (CD-ROM), for example. The computer-readable media may also be any other volatile or non-volatile storage systems. A computer-readable medium may be considered a computer-readable storage medium, for example, or a tangible storage device.

Moreover, a step or block that represents one or more information transmissions may correspond to information transmissions between software and/or hardware modules in the same physical device. However, other information transmissions may be between software modules and/or hardware modules in different physical devices.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method comprising:
   capturing, by an image sensor, a first plurality of images of a scene, wherein each image of the first plurality of images is captured using a different total exposure time (TET);
   based at least on the first plurality of images, determining a long TET, a short TET, and a TET sequence that includes the long TET and the short TET;
   capturing, by the image sensor, a second plurality of images of the scene, wherein the images in the second plurality of images are captured sequentially in an image sequence using a sequence of TETs corresponding to the TET sequence, wherein the image sequence includes a three-image sub-sequence of a first long-TET image captured using the long TET, followed by a short-TET image captured using the short TET, followed by a second long-TET image captured using the long TET; and
   based on one or more images in the image sequence, constructing an output image.

2. The method of claim 1, wherein the image sequence also includes a second three-image sub-sequence of a first third long-TET image captured using the long TET, followed by a second fourth long-TET image captured using the long TET, followed by a second short-TET image captured using the short TET.

3. The method of claim 1, wherein the image sequence includes a two-image sub-sequence of a primary short-TET image followed by a primary long-TET image, wherein the image sequence also includes one or more secondary short-TET images and one or more secondary long-TET images, wherein the primary short-TET image and the secondary short-TET images are captured using the short TET, wherein the primary long-TET image and the secondary long-TET images are captured using the long TET, and wherein constructing the output image comprises:
   forming a combined short-TET image, wherein the combined short-TET image includes the primary short-TET image and at least part of the one or more secondary short-TET images;
   forming a combined long-TET image, wherein the combined long-TET image includes the primary long-TET image and at least part of the one or more secondary long-TET images; and
   forming the output image, wherein the output image includes at least part of the combined short-TET image and at least part of the combined long-TET image.

4. The method of claim 1, wherein the image sequence includes a long-TET image captured using the long TET, and wherein constructing the output image comprises:
   determining that the long-TET image is a sharpest image of all images in the image sequence captured using the long TET;
   based on the long-TET image being the sharpest image of all images in the image sequence captured using the long TET, selecting the long-TET image as a primary long-TET image; and
   selecting, as a primary short-TET image, an image captured using the short TET that is adjacent to the primary long-TET image in the image sequence.

5. The method of claim 4, wherein constructing the output image further comprises:
- forming a combined short-TET image, wherein the combined short-TET image includes the primary short-TET image and at least part of one or more images from the image sequence that were captured using the short TET;
- forming a combined long-TET image, wherein the combined long-TET image includes the primary long-TET image and at least part of one or more images from the image sequence that were captured using the long TET; and
- forming the output image, wherein the output image includes at least part of the combined short-TET image and at least part of the combined long-TET image.

6. The method of claim 4, wherein the primary short-TET image immediately precedes the primary long-TET image in the image sequence.

7. The method of claim 6, wherein the short-TET image that immediately precedes the primary long-TET image in the image sequence is selected as the primary short-TET image based on image capture ending at the edge of respective image capture epochs.

8. The method of claim 4, wherein the primary short-TET image immediately follows the primary long-TET image in the image sequence.

9. The method of claim 8, wherein the short-TET image that immediately follows the primary long-TET image in the image sequence is selected as the primary short-TET image based on image capture beginning at the edge of respective image capture epochs.

10. An article of manufacture including a non-transitory computer-readable medium, having stored thereon program instructions that, upon execution by a computing device, cause the computing device to perform operations comprising:
- capturing, by an image sensor, a first plurality of images of a scene, wherein each image of the first plurality of images is captured using a different total exposure time (TET);
- based at least on the first plurality of images, determining a long TET, a short TET, and a TET sequence that includes the long TET and the short TET;
- capturing, by the image sensor, a second plurality of images of the scene, wherein the images in the second plurality of images are captured sequentially in an image sequence using a sequence of TETs corresponding to the TET sequence,
- wherein the image sequence includes a three-image sub-sequence of a first long-TET image captured using the long TET, followed by a short-TET image captured using the short TET, followed by a second long-TET image captured using the long TET; and
- based on one or more images in the image sequence, constructing an output image.

11. The article of manufacture of claim 10, wherein the image sequence also includes a second three-image sub-sequence of a first third long-TET image captured using the long TET, followed by a second fourth long-TET image captured using the long TET, followed by a second short-TET image captured using the short TET.

12. The article of manufacture of claim 10, wherein the image sequence includes a two-image sub-sequence of a primary short-TET image followed by a primary long-TET image, wherein the image sequence also includes one or more secondary short-TET images and one or more secondary long-TET images, wherein the primary short-TET image and the secondary short-TET images are captured using the short TET, wherein the primary long-TET image and the secondary long-TET images are captured using the long TET, and wherein constructing the output image comprises:
- forming a combined short-TET image, wherein the combined short-TET image includes the primary short-TET image and at least part of the one or more secondary short-TET images;
- forming a combined long-TET image, wherein the combined long-TET image includes the primary long-TET image and at least part of the one or more secondary long-TET images; and
- forming the output image, wherein the output image includes at least part of the combined short-TET image and at least part of the combined long-TET image.

13. The article of manufacture of claim 10, wherein the image sequence includes a long-TET image captured using the long TET, and wherein constructing the output image comprises:
- determining that the long-TET image is a sharpest image of all images in the image sequence captured using the long TET;
- based on the long-TET image being the sharpest image of all images in the image sequence captured using the long TET, selecting the long-TET image as a primary long-TET image; and
- selecting, as a primary short-TET image, an image captured using the short TET that is adjacent to the primary long-TET image in the image sequence.

14. The article of manufacture of claim 13, wherein constructing the output image further comprises:
- forming a combined short-TET image, wherein the combined short-TET image includes the primary short-TET image and at least part of one or more images from the image sequence that were captured using the short TET;
- forming a combined long-TET image, wherein the combined long-TET image includes the primary long-TET image and at least part of one or more images from the image sequence that were captured using the long TET; and
- forming the output image, wherein the output image includes at least part of the combined short-TET image and at least part of the combined long-TET image.

15. The article of manufacture of claim 13, wherein the primary short-TET image immediately precedes the primary long-TET image in the image sequence.

16. A computing device comprising:
- at least one processor;
- an image sensor;
- data storage; and
- program instructions, stored in the data storage, that upon execution by the at least one processor cause the computing device to perform operations including:
  - capturing, by the image sensor, a first plurality of images of a scene, wherein each image of the first plurality of images is captured using a different total exposure time (TET);
  - based at least on the first plurality of images, determining a long TET, a short TET, and a TET sequence that includes the long TET and the short TET;
  - capturing, by the image sensor, a second plurality of images of the scene, wherein the images in the second plurality of images are captured sequentially in an image sequence using a sequence of TETs corresponding to the TET sequence, wherein the image sequence includes a three-image sub-sequence of a first long-TET image captured using the long TET, followed by a short-TET image captured using the short TET, followed by a second long-TET image captured using the long TET; and
based on one or more images in the image sequence, constructing an output image.

17. The computing device of claim 16, wherein the image sequence also includes a second three-image sub-sequence of a first third long-TET image captured using the long TET, followed by a second fourth long-TET image captured using the long TET, followed by a second short-TET image captured using the short TET.

18. The computing device of claim 16, wherein the image sequence includes a two-image sub-sequence of a primary short-TET image followed by a primary long-TET image, wherein the image sequence also includes one or more secondary short-TET images and one or more secondary long-TET images, wherein the primary short-TET image and the secondary short-TET images are captured using the short TET, wherein the primary long-TET image and the secondary long-TET images are captured using the long TET, and wherein constructing the output image comprises:
    forming a combined short-TET image, wherein the combined short-TET image includes the primary short-TET image and at least part of the one or more secondary short-TET images;
    forming a combined long-TET image, wherein the combined long-TET image includes the primary long-TET image and at least part of the one or more secondary long-TET images; and
    forming the output image, wherein the output image includes at least part of the combined short-TET image and at least part of the combined long-TET image.

19. The computing device of claim 16, wherein the image sequence includes a long-TET image captured using the long TET, and wherein constructing the output image comprises:
    determining that the long-TET image is a sharpest image of all images in the image sequence captured using the long TET;
    based on the long-TET image being the sharpest image of all images in the image sequence captured using the long TET, selecting the long-TET image as a primary long-TET image; and
    selecting, as a primary short-TET image, an image captured using the short TET that is adjacent to the primary long-TET image in the image sequence.

20. The computing device of claim 19, wherein constructing the output image further comprises:
    forming a combined short-TET image, wherein the combined short-TET image includes the primary short-TET image and at least part of one or more images from the image sequence that were captured using the short TET;
    forming a combined long-TET image, wherein the combined long-TET image includes the primary long-TET image and at least part of one or more images from the image sequence that were captured using the long TET; and
    forming the output image, wherein the output image includes at least part of the combined short-TET image and at least part of the combined long-TET image.

21. A method comprising:
capturing, by an image sensor, a first plurality of images of a scene, wherein each image of the first plurality of images is captured using a different total exposure time (TET);
based at least on the first plurality of images, determining a long TET, a short TET, and a TET sequence that includes the long TET and the short TET;
capturing, by the image sensor, a second plurality of images of the scene, wherein the images in the second plurality of images are captured sequentially in an image sequence using a sequence of TETs corresponding to the TET sequence, wherein the image sequence includes a three-image sub-sequence of a first long-TET image captured using the long TET, followed by a second long-TET image captured using the long TET, followed by a short-TET image captured using the short TET; and
based on one or more images in the image sequence, constructing an output image.

22. A method comprising:
capturing, by an image sensor, a first plurality of images of a scene, wherein each image of the first plurality of images is captured using a different total exposure time (TET);
based at least on the first plurality of images, determining a long TET, a short TET, and a TET sequence that includes the long TET and the short TET;
capturing, by the image sensor, a second plurality of images of the scene, wherein the images in the second plurality of images are captured sequentially in an image sequence using a sequence of TETs corresponding to the TET sequence, wherein the image sequence includes a long-TET image captured using the long TET; and
based on one or more images in the image sequence, constructing an output image, wherein constructing the output image comprises (i) determining that the long-TET image is a sharpest image of all images in the image sequence captured using the long TET, (ii) based on the long-TET image being the sharpest image of all images in the image sequence captured using the long TET, selecting the long-TET image as a primary long-TET image, and (iii) selecting, as a primary short-TET image, an image captured using the short TET that is adjacent to the primary long-TET image in the image sequence.

* * * * *